(12) United States Patent
Peyman et al.

(10) Patent No.: US 9,802,165 B2
(45) Date of Patent: Oct. 31, 2017

(54) 3D EXPANDING GEOMETRY

(75) Inventors: Sally Anne Peyman, Leeds (GB); Radwa Hassan Abou-Saleh, Leeds (GB); Stephen Derek Evans, Leeds (GB)

(73) Assignee: The University of Leeds (GB)

( * ) Notice: Subject to any disclaimer, the term of this patent is extended or adjusted under 35 U.S.C. 154(b) by 828 days.

(21) Appl. No.: 14/129,574

(22) PCT Filed: Jun. 29, 2012

(86) PCT No.: PCT/GB2012/051524
§ 371 (c)(1),
(2), (4) Date: Jun. 26, 2014

(87) PCT Pub. No.: WO2013/001309
PCT Pub. Date: Jan. 3, 2013

(65) Prior Publication Data
US 2014/0321231 A1    Oct. 30, 2014

(30) Foreign Application Priority Data

Jun. 29, 2011  (GB) .................................. 1111082.2

(51) Int. Cl.
| | | |
|---|---|---|
| *B01F 3/04* | (2006.01) | |
| *B01J 13/04* | (2006.01) | |
| *B05B 1/06* | (2006.01) | |
| *B05B 7/04* | (2006.01) | |
| *A61K 9/127* | (2006.01) | |
| *A61K 9/50* | (2006.01) | |

(52) U.S. Cl.
CPC .......... *B01F 3/04985* (2013.01); *B01J 13/04* (2013.01); *A61K 9/1271* (2013.01); *A61K 9/5015* (2013.01); *B05B 1/06* (2013.01); *B05B 7/0458* (2013.01)

(58) Field of Classification Search
CPC ...... B01F 3/0446; B01J 13/04; A61K 9/1271; A61K 9/5015; B05B 1/06; B05B 1/0458
See application file for complete search history.

(56) References Cited

U.S. PATENT DOCUMENTS

2011/0045095 A1*  2/2011  Hettiarachchi ...... A61K 49/225
                                                                    424/497

FOREIGN PATENT DOCUMENTS

| JP | 2006167612 A | 6/2006 |
|---|---|---|
| JP | 2008114098 A | 5/2008 |
| KR | 100902136 B1 | 6/2009 |

OTHER PUBLICATIONS

Singhal, Vishal et al. Low REynolds number flow through nozzle-diffuser elements in valveless micropumps. Sensors and Actuators A 113 (2004) 226-235.*

(Continued)

*Primary Examiner* — Timothy Cleveland
(74) *Attorney, Agent, or Firm* — Dickinson Wright PLLC

(57) ABSTRACT

This invention relates to bubble generation, in particular to microbubble generation in a microfluidic device, which bubbles may be useful as contrasting agents or drug delivery vehicles. The invention further relates to apparatuses, systems and methods for manufacturing said microbubbles, microbubbles produced by such methods and to their uses, e.g. in medical, diagnostic and other such applications. The microbubbles are preferentially formed using a microspray regime.

24 Claims, 18 Drawing Sheets

(56) References Cited

OTHER PUBLICATIONS

Gerlach and Wurmus, "Working Principle and Performance of the Dynamic Micropump." Sens. Actuators A: Phys., 50 (1995), pp. 135-140.*

International Search Report & Written Opinion, dated Nov. 26, 2013, for PCT/GB2012/051524.

"Controllable Microfluid Synthesis of Multiphase Drug-Carrying Liposheres for Site-Targeted Therapy", Kanaka Hettiarachchi, et al; Chermical Engineers Biotechnol. Prog; Jan. 1, 2009, pp. 938-945.

"Monodispersed microfluid droplet generation by shear focusing microfluidic device", Yung-Chien Tan, et al; Sensors and Actuators B: Chemical: International Journal Devoted to Research and Development of Physical and Chemical Transducers, vol. 114, No. 1; Mar. 30, 2006, pp. 350-356.

"Formulation of Monodisperse Contrast Agents in Microfluidic Systems for Ultrasonic Imaging", Kanaka Hettiarachchi, et al; Microtechnologies in Medicine and Biology, 2006 International Conference on, IEEE, PI; May 1, 2006; pp. 230-232.

"Controlled double emuslification utilizing 3D PDMS microchannels", Fu-Che Chang, et al; Journal of Micromechanics & Microengineering, Institute of Physics Publishing, vol. 18, No. 6; Jun. 1, 2008; p. 65018.

* cited by examiner

3D EXPANDING GEOMETRY

CROSS-REFERENCE TO RELATED APPLICATIONS

The present application is a 35 U.S.C. Section 371 national stage filing of International Patent Application No. PCT/GB2012/051524, filed 29 Jun. 2012, and through which priority is claimed to UK application GB 1111082.2, filed 29 Jun. 2011, the disclosures of which are incorporated herein by reference in their entireties.

This invention relates to bubble generation, in particular to microbubble generation in a microfluidic device, which bubbles may be useful as contrasting agents or drug delivery vehicles. The invention further relates to apparatuses, systems and methods for manufacturing said microbubbles, microbubbles produced by such methods and to their uses, e.g. in medical, diagnostic and other such applications.

It is known in the prior art that microbubbles, by which is meant bubbles having a diameter of less than 20 µm, preferably less than 15 µm, may be used as ultrasound contrasting agents or as drug delivery vehicles. In brief a microbubble will have a gas core, a shell material surrounding the core and may carry an active.

The gas core of an ultrasound contrast microbubble determines the 'echogenicity'. When gas bubbles are caught in an ultrasonic frequency field, they compress, oscillate, and reflect a characteristic echo. This echo generates a strong and unique sonogram. Gas cores can be composed of air or nitrogen, or heavy gases like fluorocarbon. Heavy gases are less water-soluble so they are less likely to leak out from the microbubble to impair echogenicity. Therefore, microbubbles with heavy gas cores are likely to last longer in circulation.

The shell material affects microbubble mechanical elasticity. The more elastic the material, the more acoustic energy it can withstand before bursting. Currently, microbubble shell materials may be composed of albumin, galactose, lipid, or polymers.

It is possible to control the movement of a microbubble using sonography. This property also makes microbubbles potentially very useful in the delivery of actives to a site of use.

It is known that actives can be provided either within a microbubble or on a microbubble. For example chemotherapeutic agents can be bound to a bubble for targeted release within a body.

The provision of monodisperse populations of microbubbles is beneficial because the interaction with ultrasound radiation can more efficient. Moreover, the capacity of radiation to cause motion in microbubbles is likely to be more effective with a monodisperse population and a particular frequency. The disruption (i.e. collapse) of the bubbles is improved when using a single frequency.

A further advantage with monodisperse populations is that a larger amount of bubbles from a population can access a particular site of use, for example, through capillaries in the human body, or entering tissue.

Monodisperse in this context means a population of microbubbles in which a high proportion of generated microbubbles have a diameter which is within a single standard deviation of the mean and wherein the standard deviation is small when compared to the mean.

Another factor is to be able to generate microbubble populations quickly enough so that an effective amount can be generated in a (clinically—diagnostically or therapeutically) sensible time period. The generation of monodisperse populations and fast generation are typically in competition.

US 2009098168 discloses a microfluidic apparatus and method for manufacturing microbubbles, which microbubbles can contain therapeutic agents and can comprise a plurality of shell layers. The method permits manufacture of a monodisperse microbubble population, but the production rates and the quantity of microbubbles produced is low and hence is of extremely limited relevance in a clinical or commercial context.

It is an object of the present invention to obviate or at least mitigate at least some of the problems associated with the prior art.

A first aspect of the invention provides a nozzle for receiving and/or generating microbubbles in a microfluidic device, the nozzle having an entry orifice and extending along a longitudinal axis from the orifice to define a microbubble flow direction, the nozzle having a width and a height dimension both of which increase in the bubble flow direction.

Preferably, the width and/or the height dimensions increase discretely, for example in a step-wise fashion. The width and/or height dimensions may increase at one or more distinct axially separate locations.

Additionally or alternatively, the width and/or height dimensions increase continuously, for example in a pyramidal or conical form.

The width and height dimensions may increase at different axial locations or at different points in the flow direction.

In a one embodiment the nozzle comprises, a region where the width increases proximal to the entry orifice but the height remains substantially constant, followed by a region where the height increases.

Such a nozzle is particularly well adapted for use in a microspray method of microbubble generation, which will be described in more detail below.

The entry orifice may have any suitable shape, e.g. it may be round, square, rectangular or the like. Preferably the entry orifice provides an opening which is 30 µm or less at its widest point, more preferably from 2 to 20 µm, more preferably from 5 to 15 µm. For example a suitable orifice has a rectangular shape, having a width of 10 µm and a height of 15 µm. It is generally preferred that the orifice is smaller than in conventional microbubble generation devices such as those of US 2009098168. A smaller orifice is well adapted to use in a microspray microbubble generation method as discussed in detail below.

A second aspect of the invention provides microfluidic apparatus for the generation of microbubbles, the apparatus comprising one or more gas flow conduits, one or more liquid flow conduits, a contact chamber and a nozzle, the contact chamber having an orifice in communication with the nozzle along which, in use, bubbles flow, the nozzle having a width and height dimension which increase in the bubble flow direction.

In a preferred embodiment the apparatus comprises a pair of liquid flow conduits which discharge into opposite sides of the contact chamber, and a gas flow conduit which discharges into the contact chamber between the discharge points of the liquid flow conduits. Preferably the gas flow conduit is aligned with the bubble flow direction when it meets the contact chamber, and the liquid flow conduits are angled relative to the bubble flow direction when they meet the contact chamber. The gas flow conduit can be orthogonal to the two liquid flow conduits. For example the gas flow conduit and the liquid flow conduit can meet in the general form of a T, with the liquid flow conduits substantially perpendicular to the gas flow conduit, and the gas flow conduit being aligned with the bubble flow direction. Alternatively the liquid flow conduits could meet at 45 degrees or any other suitable. Thus it can be seen that the contact chamber acts as a point of convergence in flow focussing of the gas and liquid flow conduits. In use gas continues along its direction of flow into the orifice for microbubble generation in association with the liquid flows coming in from the sides. It will be apparent that there are many possible configurations of the various conduits where they coincide at the contact chamber, and the invention embraces any configurations which result in suitable microbubble generation.

Conveniently the gas and liquid flow conduits have a square or rectangular cross section, because this allows for simple manufacturing using conventional photolithography techniques. However, it is perfectly possible that other shapes could be used, and indeed may be desirable to improve flow characteristics of the relevant fluids. The conduits can vary in their dimensions along their length. When considering the effects of the dimensions of the various conduits it is primarily their dimensions as they reach the point of entry into the contact chamber which is of most importance. Exemplary dimensions for rectangular liquid flow conduits as to they arrive at the contact chamber are 50 μm wide and 25 μm deep. Exemplary dimensions for the gas flow conduit as it arrives at the contact chamber is 35 μm wide and 25 μm deep, and typically it tapers to this width. Selecting suitable shapes and dimensions for any particular application would be a matter of routine optimisation.

Optionally the apparatus can comprise one or more secondary liquid flow conduits to carry a further liquid component to form an additional layer in or on the microbubbles. The secondary flow conduits can discharge directly into the contact chamber, e.g. at a location between the (primary) liquid flow conduits and the gas flow conduit. Alternatively, the secondary flow conduits can discharge into the (primary) flow conduits before they discharge into the contact chamber. In the latter configuration, the secondary flow conduit is preferably adapted to intersect the (primary flow conduit) in a manner which allows the secondary fluid and primary fluid to maintain separate laminar flow.

Further additional liquid flow conduits could be added, e.g. tertiary and quaternary flow conduits to allow additional components to be added to the microbubbles.

In a preferred embodiment there is provided a multiplex microfluidic apparatus comprising a plurality of contact chambers, nozzles and associated liquid and gas flow conduits. A multiplex arrangement provides a convenient arrangement for increasing rates of microbubble production.

The apparatus may further comprise a source of gas and a gas flow controller to control flow of the gas to the contact chamber, and a source of liquid and a liquid flow controller to control flow of said liquid to the contact chamber.

In a preferred embodiment the apparatus is configured to produce microbubbles in a microspray regime. In particular the apparatus can be configured such that in use a bulb of gas extends from the gas flow conduit at least into the orifice and preferably through the orifice and into the nozzle. More preferably the gas bulb extends to a region where the height and width dimensions of the nozzle increase.

The apparatus can be so configured by adjusting the pressure of the gas supplied to the contact chamber and the flow rate of the liquid to cause microspray microbubble generation.

In a further aspect there is provided a kit comprising:

At least one microfluidic apparatus for the generation of microbubbles, the apparatus comprising one or more gas flow conduits, one or more liquid flow conduits, a contact chamber and a nozzle, the contact chamber having an orifice in communication with the nozzle along which, in use, bubbles flow, the nozzle having a width and height dimension which increase in the bubble flow direction a source of gas;

a gas flow controller to control flow of the gas to the contact chamber;

a source of liquid; and a liquid flow controller to control flow of said liquid to the contact chamber.

A further aspect of the invention provides a method of generating a population of microbubbles, the method comprising using the nozzle and/or apparatus of the first and/or second aspects of the invention.

The method of the invention can be used to produce a monodisperse or near monodisperse microbubble population in a clinically (e.g. therapeutically or diagnostically) appropriate timeframe. In a particularly preferred embodiment the microbubbles produced have a dispersity index which is less than 100%, preferably 50% or less and most preferably 35% or less.

The method suitably comprises providing a microbubble forming liquid though at least one liquid flow conduit and a gas via at least one gas flow conduit.

The microbubble forming liquid comprises one or more materials suitable to form microbubble shells containing a gas core, i.e. the gas provided by the gas flow conduit, in a carrier liquid. Suitable materials to form the microbubbles include a wide range of amphiphilic molecules which are able to self-assemble into a microbubble shell. Mention can be made of amphiphilic lipids, such as modified or unmodified phospholipids, which are particularly preferred components. Alternatively, amphiphilic polymers could be used, such as natural or synthetic proteins or peptides, synthetic or natural polymers (including block co polymers). The liquid can suitably be an aqueous dispersion, solution or emulsion of the materials, although other liquid media could be used as appropriate.

The gas provided by the gas flow conduit can be any suitable gas or mixture of gases for forming microbubbles. Gases which are insoluble or poorly soluble in the liquid medium in which the bubbles will be formed are preferred. As this medium is commonly aqueous, it is generally preferred to use gases which are insoluble or poorly soluble in water. A typical gas used in manufacturing microbubbles is octafluoropropane, and this is well suited to the present invention. However, it should be realised that there are a wide variety of gases that can be used depending on the intended use of the microbubbles and various possible shell materials and media.

In a particularly preferred embodiment the method comprises providing the gas in such a manner that the bulb of gas formed in the contact chamber extends into the orifice between the contact chamber and the nozzle, and thereby forms microbubbles in the nozzle. More preferably the gas bulb extends through the orifice and projects into the nozzle. Most preferably the gas bulb extends to, or near to, a region where the height dimension of the nozzle increases. In such a method microbubbles are believed to be formed in great numbers by the action of shear forces and turbulence in combination with the pressure drop caused by exit of the orifice. Where this pressure drop is increased as a result of the expansion of the nozzle in both width and height the production of microbubbles is greatly increased. Thus, the combination of extending the gas bulb into, and preferably beyond, the orifice combined 3D nozzle expansion results in a greatly improved mechanism of microbubble formation.

This improved mechanism of microbubble formation by extending the gas bulb into and beyond the orifice has been termed 'microspray', and this term will be used at various points in the following text. Bubbles are formed in large numbers as a 'spray' rather than one-by-one. By providing a region of significant pressure drop, i.e. as achieved using an expansion of the nozzle in both width and depth, it appears that the microspray method can be enhanced further and thus produce far greater quantities of microbubbles than prior microfluidic devices. This method thus differs significantly from known microfluidic microbubble generation methods in which individual bubbles are nipped off at the entrance to the orifice due to impingement of the gas by lateral lipid flows.

Preferably the population of microbubbles generated has a mean diameter of 10 µm or less, more preferably 8 µm or less, yet more preferably from 0.1 to 8 µm, most preferably from 0.5 to 5 µm. It will be appreciated that microbubbles are typically substantially spherical in shape and thus a typical bubble will typically have a true 'diameter' because it is spherical. However, there may be instances where microbubbles are somewhat irregular in shape, and, for clarity, in such instances 'diameter' is used in the sense of the diameter of a sphere which has the same volume to the particle—thus, in these circumstances the relevant measurement can be termed the 'sphere volume equivalent diameter'.

Preferably the method produces a population of microbubbles which has a dispersity index (as defined in more detail below) that is 100% or less, preferably 50% or less and most preferably 35% or less. Such a dispersity index is indicative of monodisperse or nearly monodisperse microbubbles, with lower disparity index representing a less disperse population. Such microbubbles are well adapted for use in ultrasound imaging and for other medical and diagnostic purposes.

Suitably the liquid flow rate is from 1 to 100 µL min$^{-1}$, preferably from 5 to 75 µL min$^{-1}$, and more preferably from 10 to 30 µL min$^{-1}$. This total flow rate may in some embodiments be split between two or more liquid flow conduits which discharge into the contact chamber.

Suitably the gas pressure is from 1 to 100 psi, preferably from 5 to 50 psi, and more preferably from 10 to 30 psi.

It will be apparent that the flow rates and pressures referred to above are specified in relation to the flow rate and pressure at, or just before, the point the gas and fluid focus at the contact chamber. Where, for example, there is provided a multiplex chip, the total flow rate from the source of liquid may be higher, this total flow being subsequently divided between the various individual microbubble generators. Likewise, there may be a change in pressure between the source of gas and the contact chamber, e.g. due to multiplex arrangements and variations in size and shape of conduits.

In certain embodiments a flow rate of approximately 20 µL min$^{-1}$ and a pressure of approximately 12.5 psi have been found to result in particularly high microbubble yields. However, it will be apparent to the skilled person that selecting appropriate pressures and flow rates will be a matter for routine optimisation depending on the various gases and liquids being used.

The method suitably comprises providing a linker moiety such that the microbubbles comprise the linker moiety. The linker moiety is preferably provided in a flow of liquid. The linker can conveniently be provided in a combined liquid flow along with the material to form the shell of the microbubble. Suitably the linker moiety is provided in the shell of the microbubble, e.g. the linker moiety is at least partially incorporated into the microbubble shell. A preferred linker moiety is an amphiphilic moiety wherein the linker functionality is provided on the hydrophilic portion of the moiety. For example, the linker moiety may comprise a lipid moiety or having linker functionality provided on the head group. A wide variety of suitable amphiphilic moieties are known and several examples are described in detail below. Conveniently the amphiphilic linker moiety can be provided in the liquid flow in combination with the lipid, and is thus incorporated in the lipid microbubble shell.

In one embodiment the method comprises providing liposomes to the microbubble. Suitably the liposomes are linked to the microbubble via a linker and a corresponding linker provided on the liposome. In one embodiment liposomes can be introduced in a combined liquid flow along with the material which forms the shell of the microbubble. The liposomes are thereby linked to the shell of the microbubbles. A significant advantage of this is that liposome attachment can be achieved in a single step during microbubble formation. It has been surprisingly found that very high efficiency linking of liposomes to microbubbles can be achieved in a single step, with no need for a further washing step to take place to remove significant quantities of unbound liposomes.

Preferably the method comprises providing a hydrophobic liquid phase such that the microbubbles produced comprise the hydrophobic liquid phase. Optionally the hydrophobic liquid phase is provided in a manner such that it is included within the microbubble, i.e. inside the shell layer of the microbubble. Alternatively, the hydrophobic liquid phase can be provided in a manner such that it is included outside of the microbubble, i.e. outside of the shell layer of the microbubble. The hydrophobic liquid component can suitably comprise an oil.

Where the hydrophobic liquid phase is internal, it can suitably form an internal layer within the microbubble, e.g. a layer of oil which lies inside the shell of the microbubble which interacts with the hydrophobic tails of lipids forming the shell. To form microbubbles with an internal hydrophobic phase, the method can suitably comprise introducing a flow of a suitable hydrophobic liquid phase to the contact chamber. Preferably the flow of the hydrophilic liquid phase is introduced such that when it meets the gas and the liquid phase comprising the shell material it is positioned between the gas and the liquid phase comprising the shell material.

Where the hydrophobic liquid phase is external it can suitably comprise a plurality of droplets comprising the hydrophobic liquid phase which are linked to the shell of the microbubble. Suitably the droplets comprise linker moieties via which they are linked to linker moieties on the microbubbles. Suitably the droplets comprising linker moieties can be introduced in a combined liquid flow along with the material which forms the shell of the microbubble. The droplets are thereby linked to the shell of the microbubbles. As with liposomes, very efficient single step incorporation of such droplets can be achieved.

It should be noted that, in addition to liposomes and oil droplets, a wide variety of particles can be linked to the microbubble. Other particles of interest include polysomes, virus particles, other forms of membrane bound particles, and the like.

Preferably the method comprises providing an active agent to the microbubbles. The active agent can be a therapeutic, diagnostic or labelling agent. Where the therapeutic agent is a hydrophobic component it can conveniently be provided in a hydrophobic liquid phase.

Suitably the method comprises providing a targeting moiety to the microbubbles, e.g. an antibody, antibody fragment, receptor, receptor ligand or any other suitable targeting moiety. Suitably the targeting moiety comprises a linker moiety adapted to link the targeting moiety to a linker moiety provided on the microbubble.

Suitably the method comprises providing a label to the microbubble. Preferably the label is a fluorophore, chromophore or radiolabel. Suitable fluorophores include fluorescent proteins or quantum dots (QD). The label can be linked to the shell of the microbubble, e.g. via a linker or by being integrated into a lipid which is incorporated into the shell.

Suitably the method comprises providing one or more magnetic or charged particles to the microbubbles.

In a further aspect the invention provides a composition comprising microbubbles produced by any one of the methods described above.

In one embodiment the composition is the direct output from the method described above. Suitably the composition comprises a population of microbubbles at concentration of $10^8$ or higher MB mL$^{-1}$, for example from $10^8$ to $10^{11}$ MB mL$^{-1}$.

In another embodiment the composition is a pharmaceutical or diagnostic composition.

In a further aspect the invention provides the use of such microbubbles for therapy or diagnosis.

In order that the invention may be more fully understood, it will now be described, by way of example only, and with reference to the accompanying drawings, in which.

Figure 8:
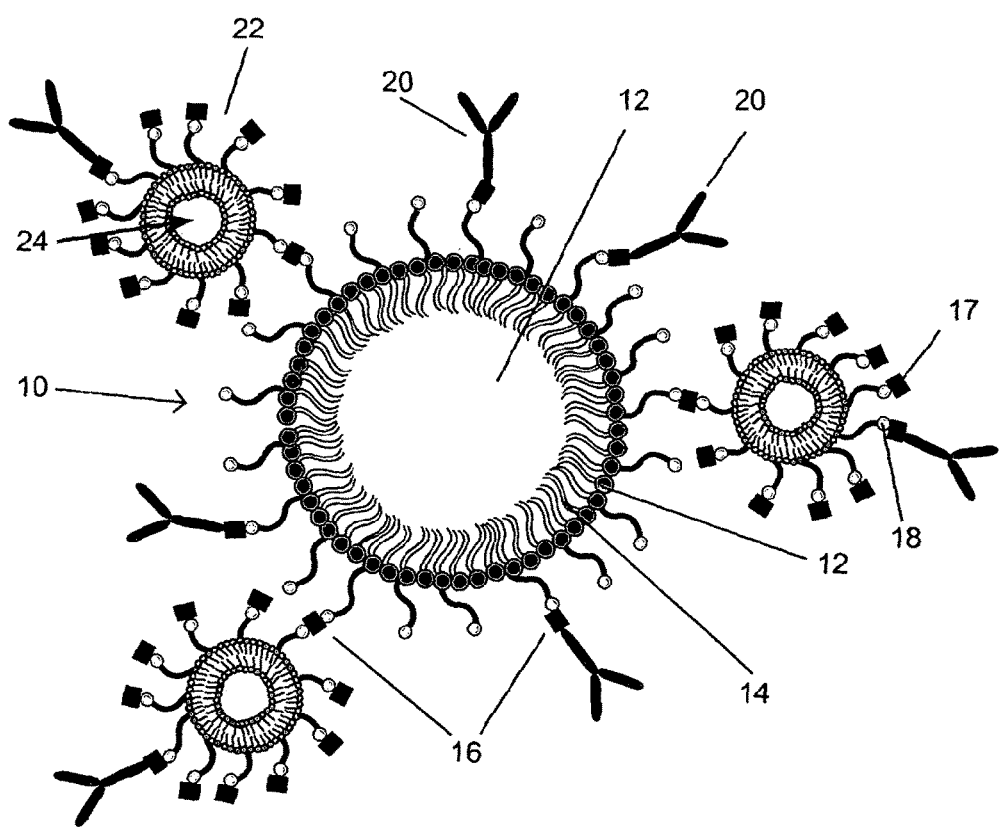
Figure 9:
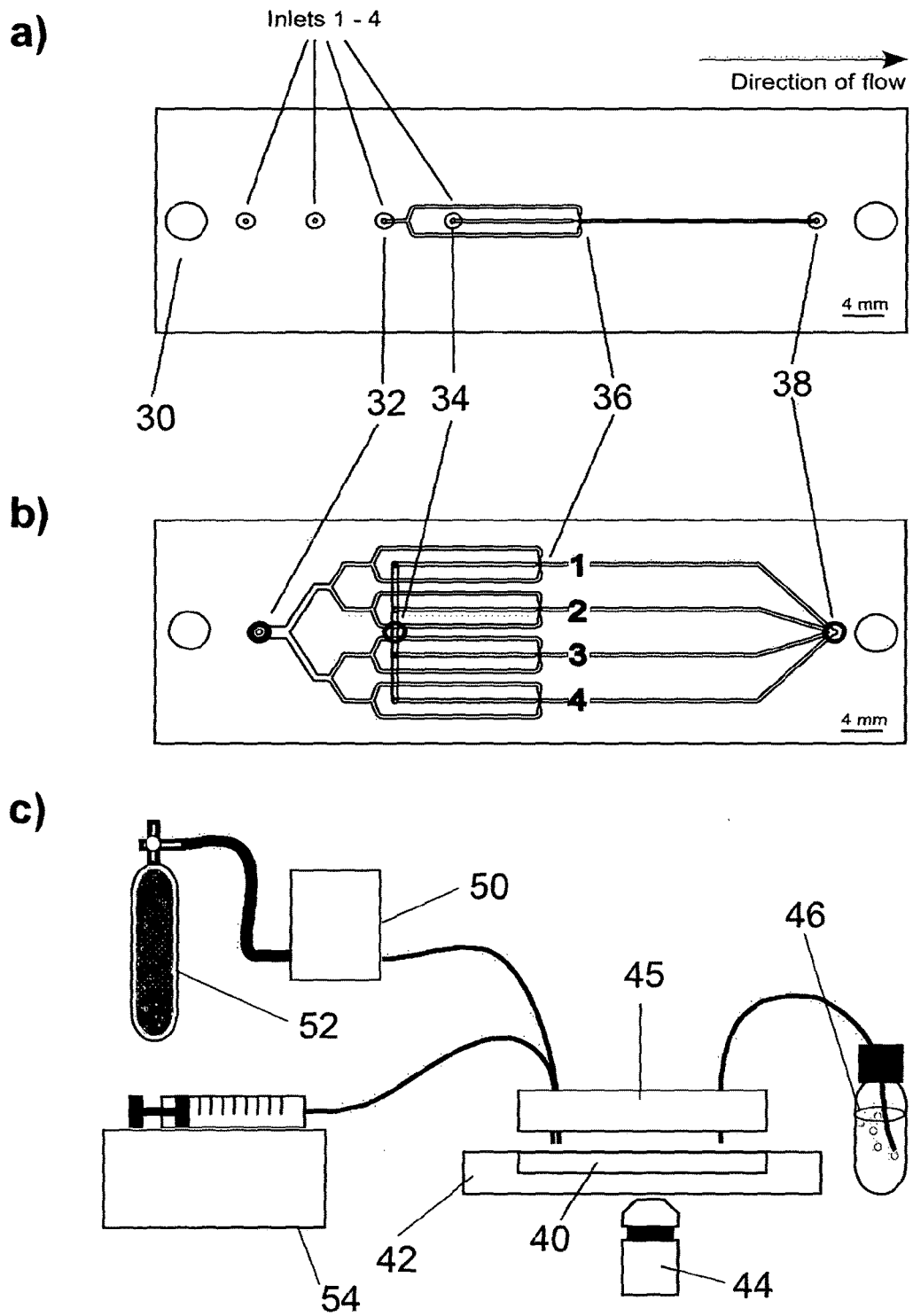
Figure 10:
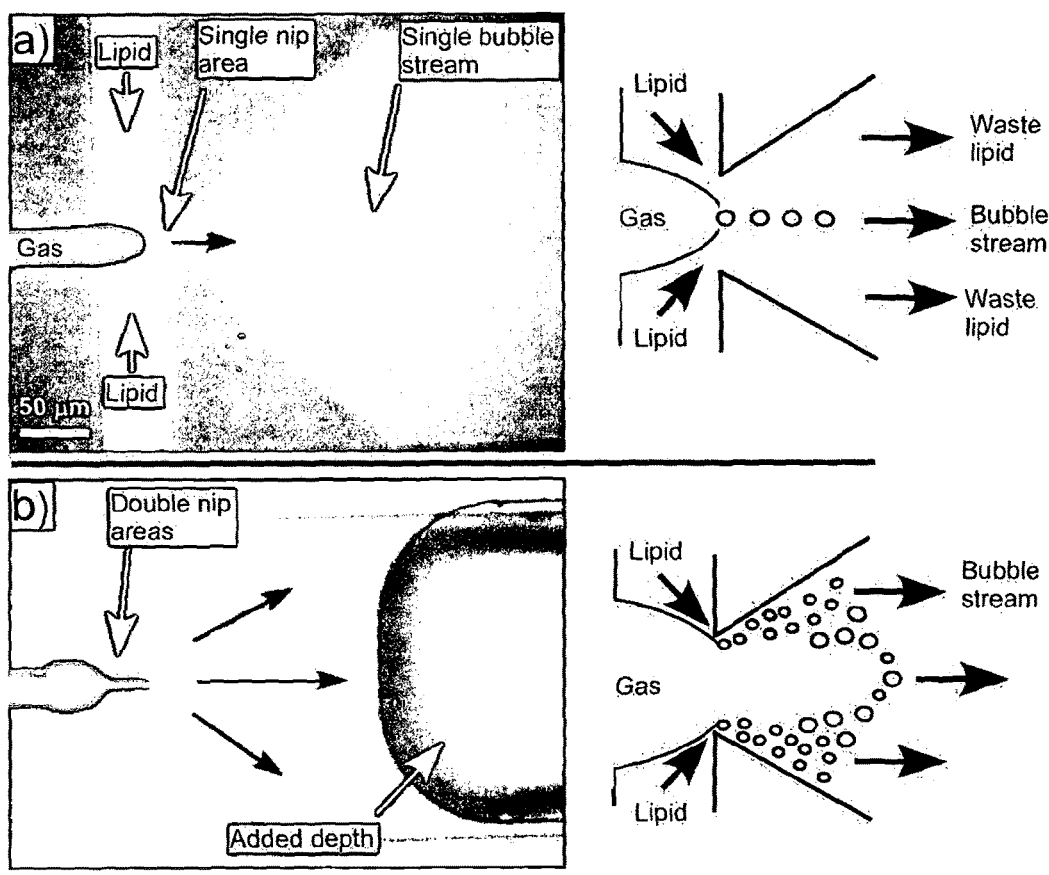
Figure 11:
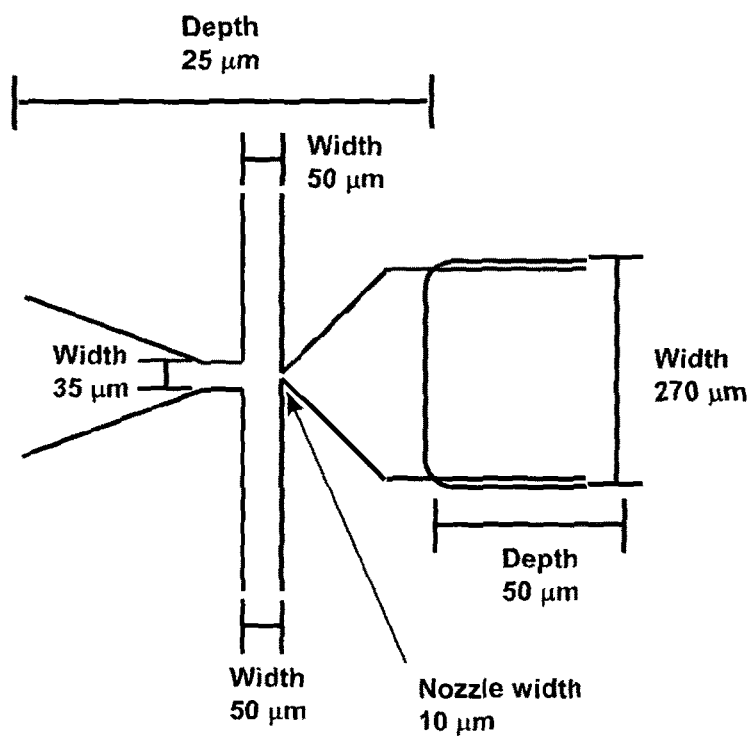
Figure 12:
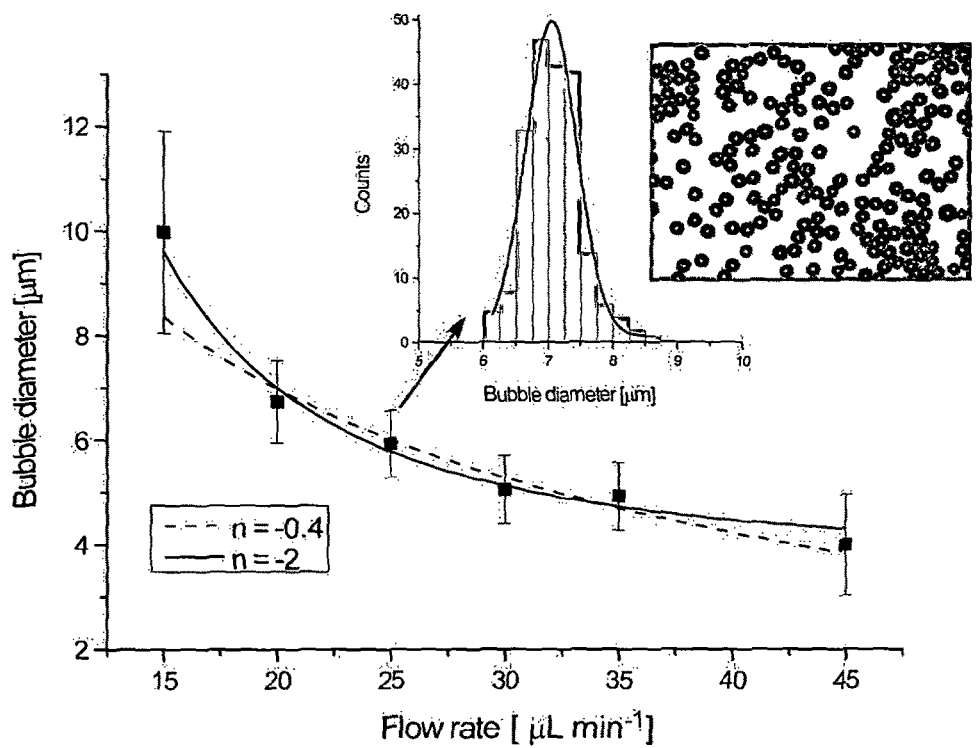
Figure 14:
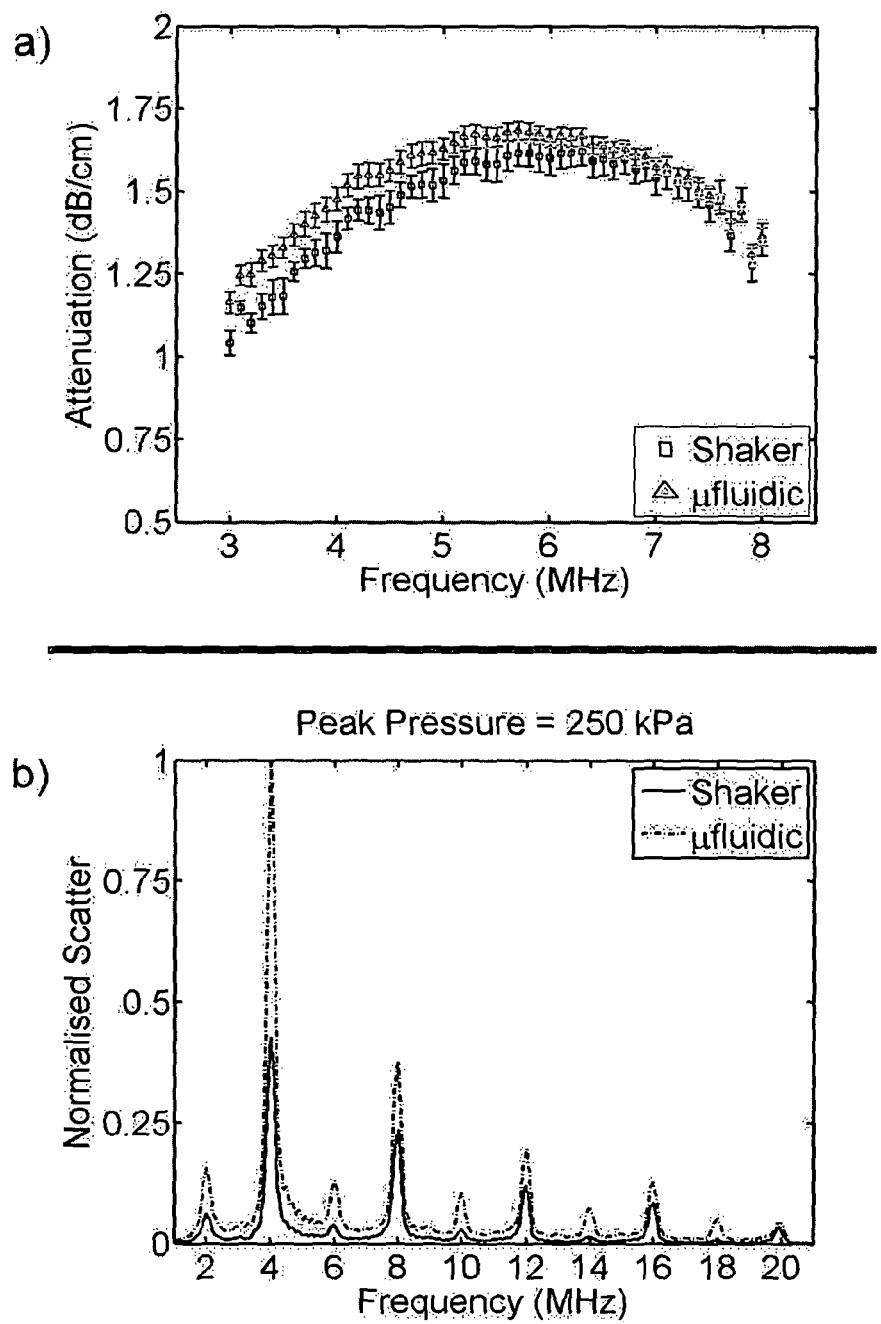
Figure 15:
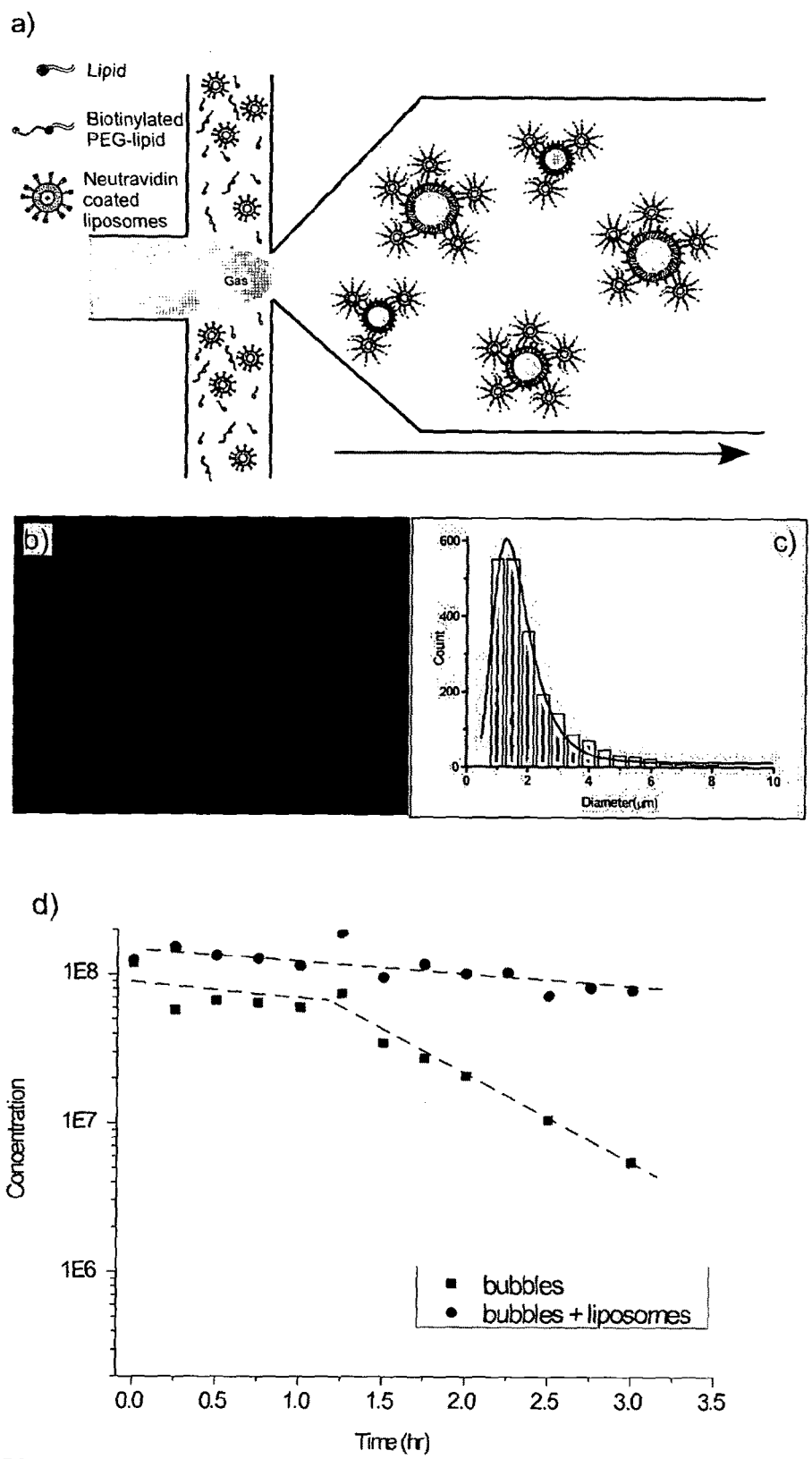
Figure 16:
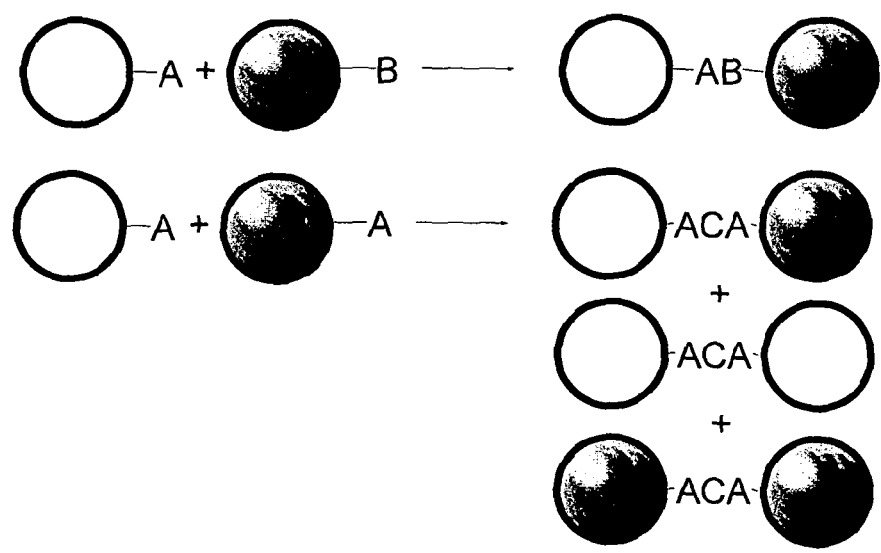
Figure 17:
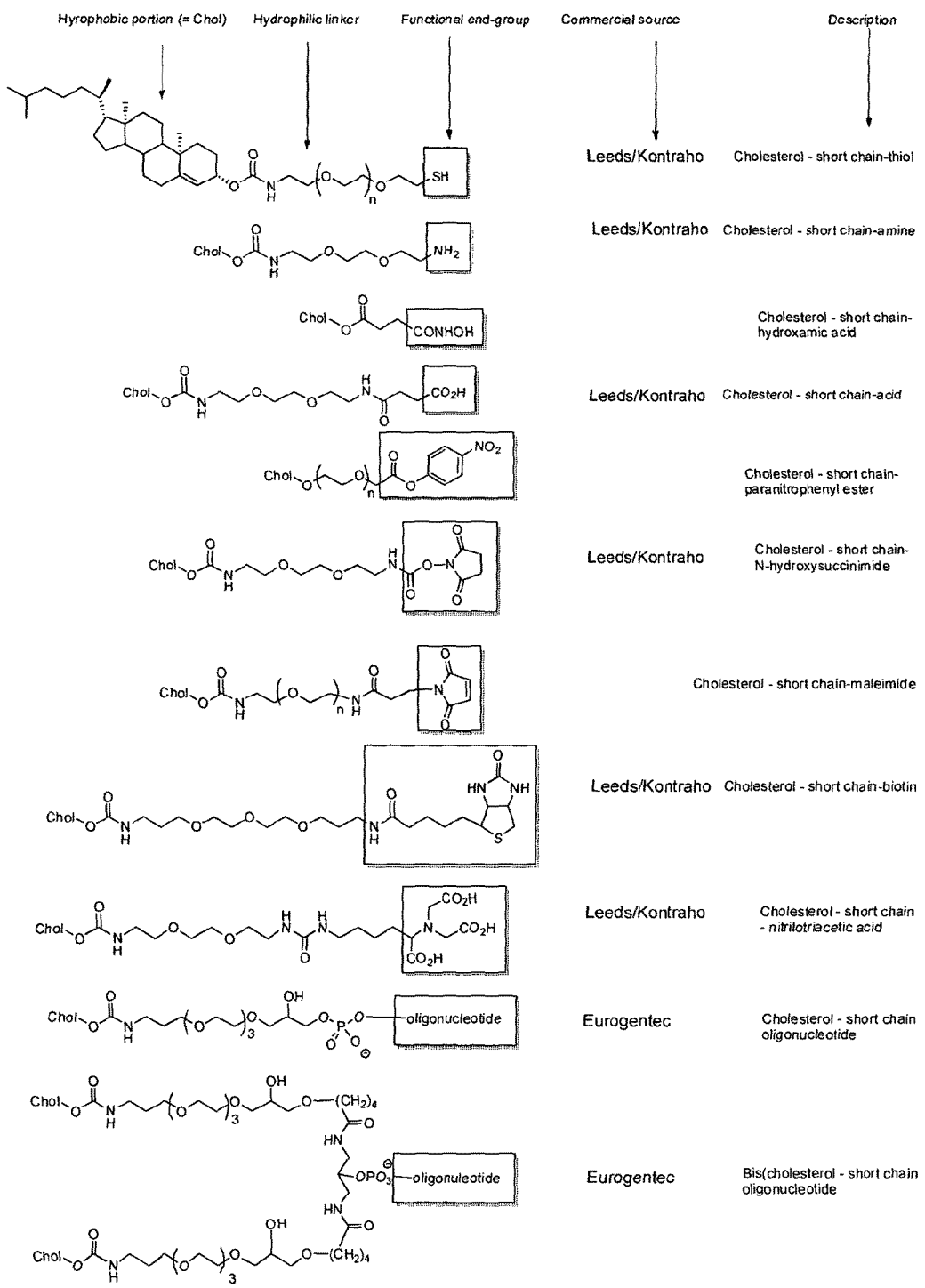
Figure 18:
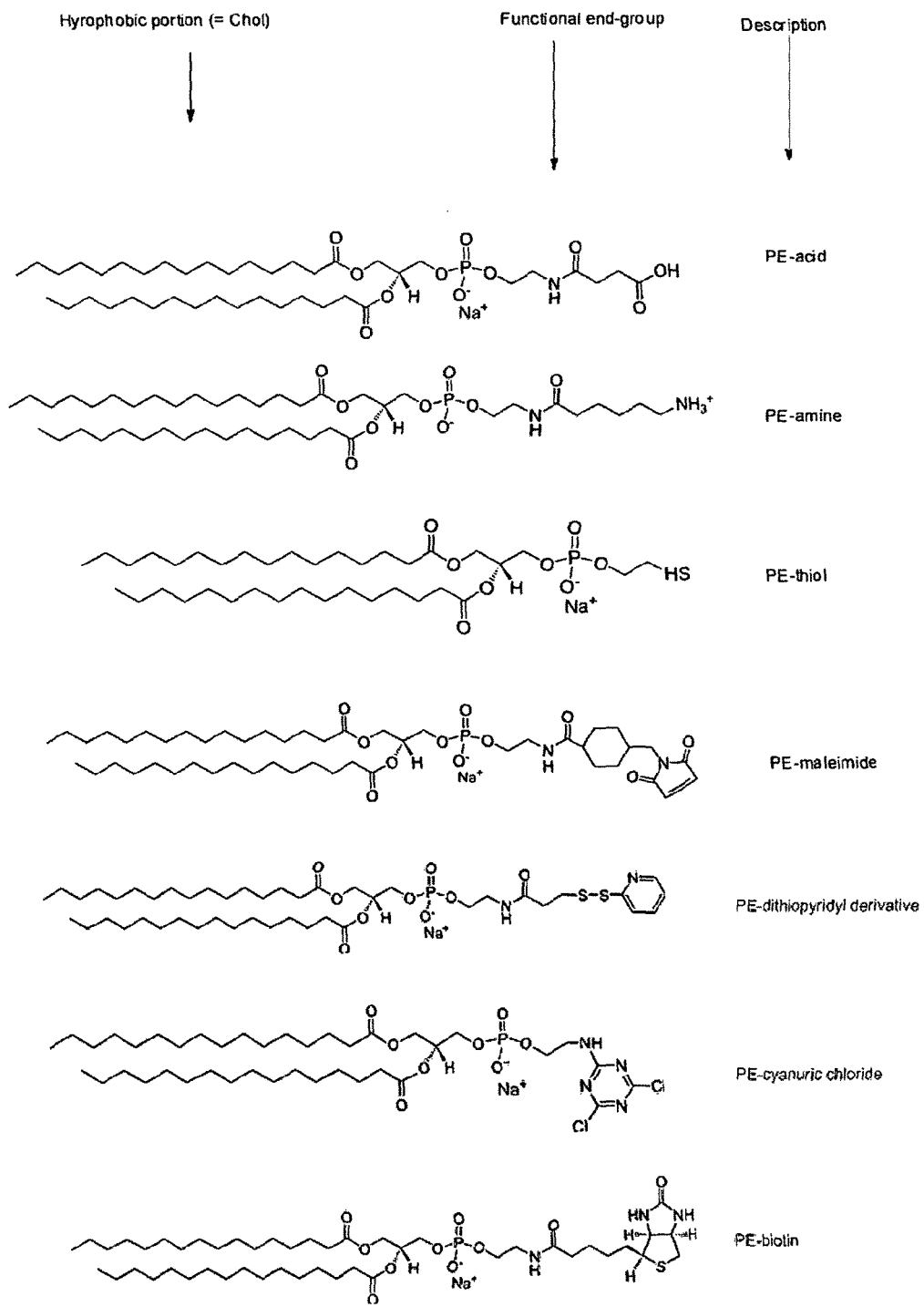
Figure 19:
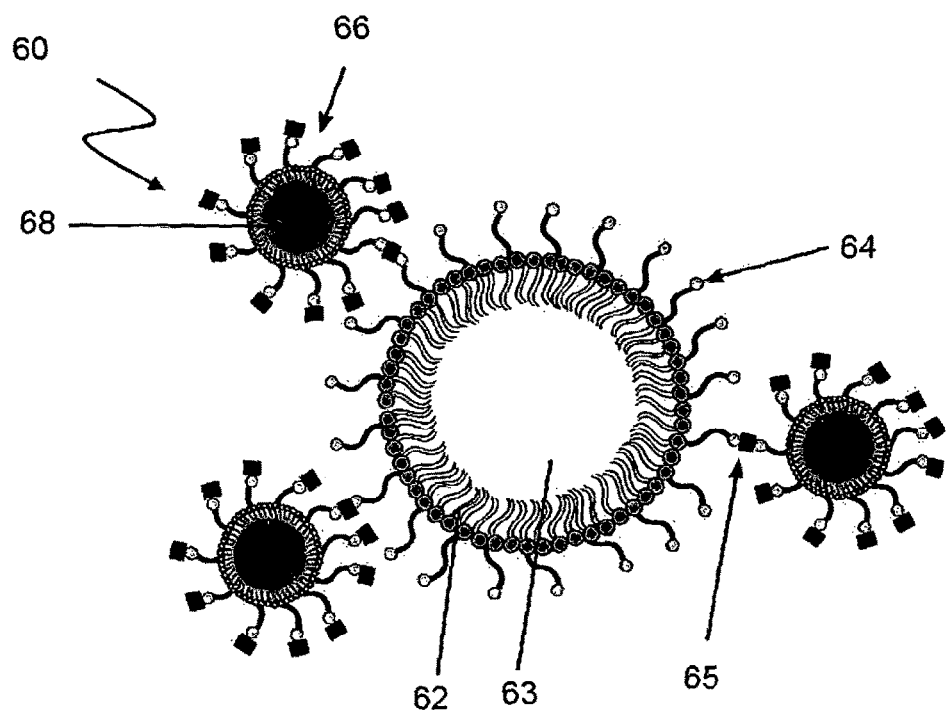
Figure 20:
Figure 22:
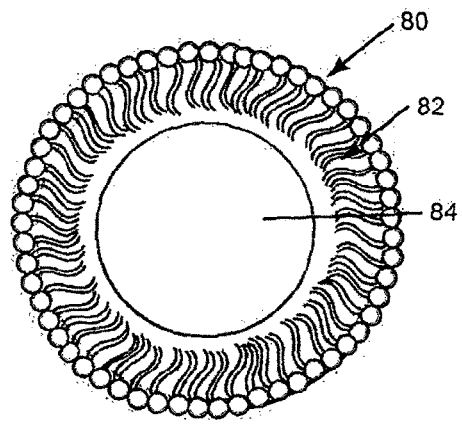
Figure 23:
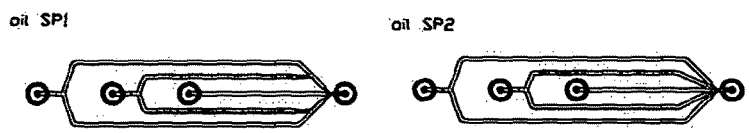
Figure 24:
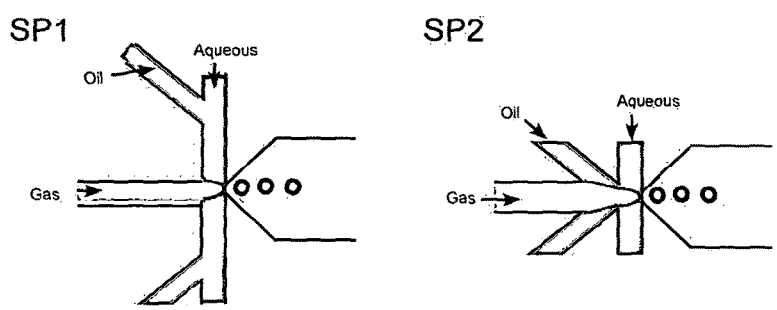
Figure 25A:
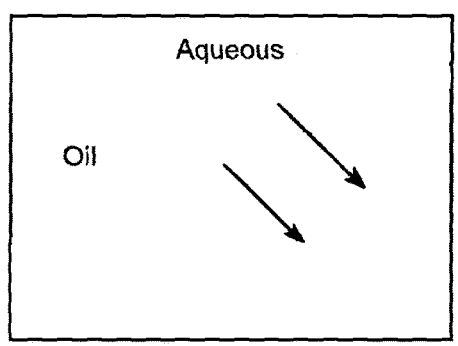
Figure 25B:
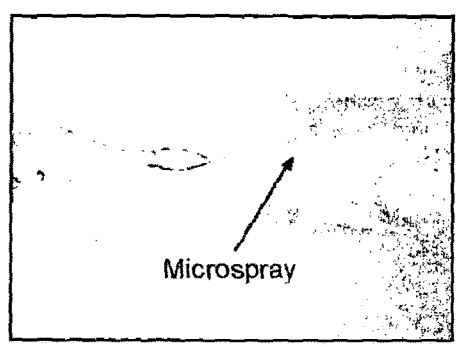
Figure 26A:
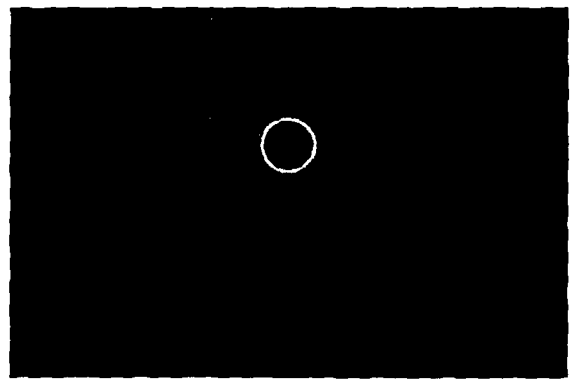
Figure 26B:
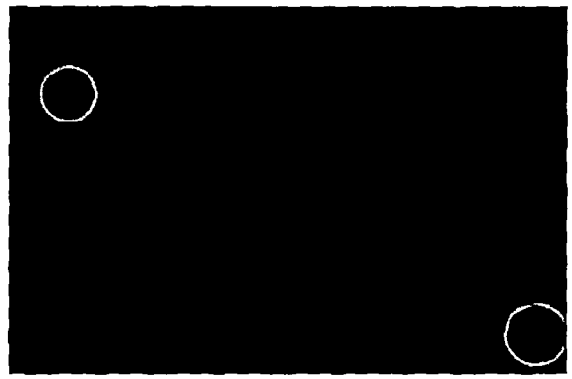
Figure 26C:
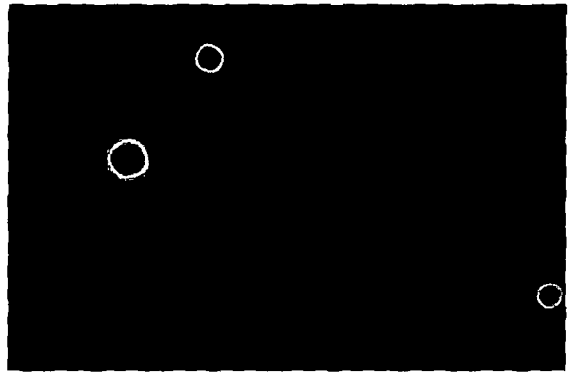

FIG. 8 shows a schematic of a therapeutic microbubble consisting of a lipid coated MB (with PEG shell) plus a layer of delivery capsules (e.g. lipo-/polymer-somes. The delivery vehicles contain antibodies for targeting, e.g. to diseased cells. The figure is not to scale, the liposomes would be 100-200 nm in diameter and would cover the entire bubble surface, whilst the MB would be say 1-2 microns in diameter;

FIG. 9 shows (a) a schematic representation of an embodiment of the present invention, (b) a schematic representation of an embodiment of the invention comprising a multiplexed microchip having 4 modules, and (c) a schematic representation of a set up according to the present invention including a gas flow controller, syringe pump, microchip stage, manifold and collection vial (not to scale);

FIG. 10 shows photograph and schematic representations of (a) formation of the monodisperse bubble regime showing the single nip area in the nozzle of a conventional device, and (b) a new, higher-rate formation of microbubbles indicating formation immediately downstream of the nozzle in accordance with the present invention;

FIG. 11 shows a diagram of an apparatus according to the present invention with dimensions shown;

FIG. 12 shows a line graph of variation of bubble size with increasing liquid flow rate, $Q_l$, at constant gas pressure=5 psi. An insert in the figure shows a histogram of microbubble size distribution at $Q_l$=20 μL min$^{-1}$ (RSD at this flow rate was ~6%) and an image of the bubble population at 60× magnification;

FIG. 13 shows (a) the relationship between microbubble concentration [bubbles mL$^{-1}$] with increasing liquid flow rate; the optimum bubble concentration of $1\times10^9$ bubbles mL$^{-1}$ was obtained at $Q_l$=20 μL min$^{-1}$, and (b) a histogram showing microbubble populations from microfluidic microspray regime (red) and from mechanical agitation (blue)— RSD for the two techniques are 50% and 55%, respectively, however the mechanical agitation produced a small number of very large bubbles (>20 μm). These were not included in the histogram;

FIG. 14 shows (a) the averaged attenuation cm$^{-1}$ of microbubbles of the present invention over a frequency range of 3-8 MHz, and (b) scatter from microbubbles generated by the traditional mechanical agitation method and from the microfluidic formation. Scatter for microfluidic microbubbles is approximately twice that of mechanical agitation;

FIG. 15 shows (a) a schematic of the one-step surface functionalisation of microbubbles with liposomes, (b) a fluorescence image of microbubbles functionalised with liposomes containing QDs, (c) a histogram showing functionalised microbubble size distribution—bubbles do not exceed 10 μm in diameter, and (d) microbubble lifetimes for a microbubble population functionalised with liposomes (red) and an un-functionalised population (black)—microbubbles with liposomes attached to their surface have a longer lifetime than microbubbles with the lipid shell alone at room temperature;

FIG. 16 illustrates directional and non-directional coupling of microbubbles via linkers;

FIGS. 17 and 18 show a variety of linker molecules for use in the present invention;

FIG. 19 shows a schematic of microbubble loaded with lipid coated oil nano droplets;

FIG. 20 shows lipid oil nano-droplets (LOND) coated microbubbles during formation at 14 psi, 30 μL/min in 3D expansion chip;

FIG. 21 shows LOND coated microbubbles with a 'halo' of green (fluorescence due to fluorescein in the oil) around their periphery;

FIG. 22 shows a microbubble with an internal oil layer for hydrophobic drug delivery;

FIG. 23 shows schematics of two designs (SP1 and SP2) for preparation of the oil microbubbles;

FIG. 24 shows schematic of the two designs of FIG. 22 (SP1 and SP2) with the introduction of the different phases shown in greater detail;

FIG. 25 shows SP1 microspray regime forming the microbubbles containing the oil layer (gas at 14 psi, oil 2 μL/min, lipid aqueous 30 μL/min). Whilst the bubbles were formed with the microspray regime (i.e. gas bulb extending into the nozzle), the design did not benefit the 3D nozzle expansion at this time for ease of manufacture, but such modification would significantly improve bubble formation;

FIGS. 26a to 26c show fluorescent images of the microbubbles produced. The oil layer inside the bubbles contains the fluorescent label fluorescein.

Figure 1:
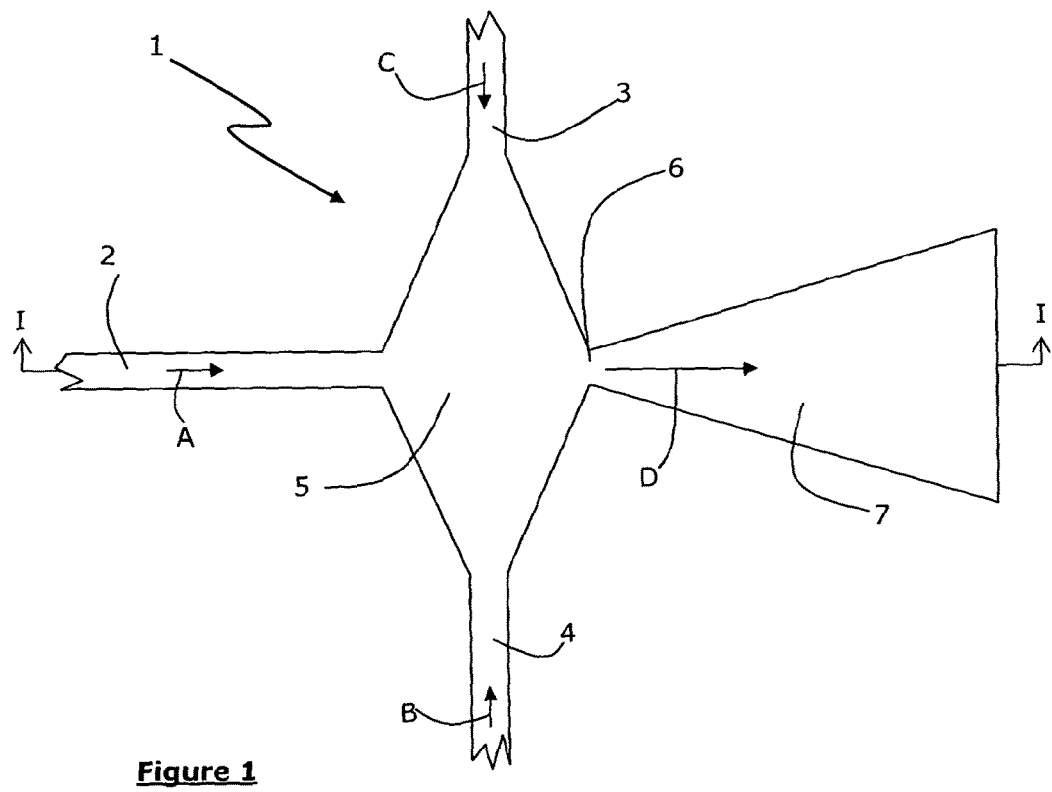
FIG. 1 shows a plan view of a first embodiment of the invention.
Figure 2:
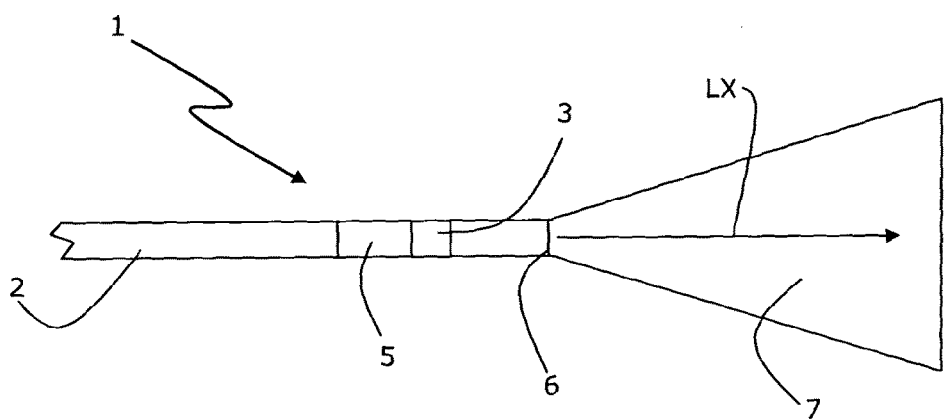
FIG. 2 is a sectional view of FIG. 1 along the line I-I.
Figure 3:
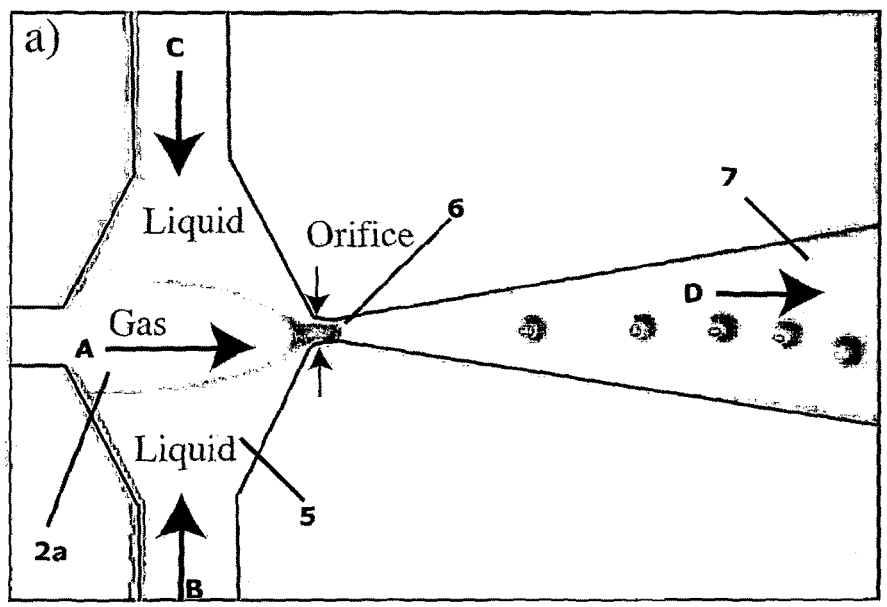
FIG. 3 is a cutaway view of FIG. 1.

Referring to FIGS. 1, 2 and 3 there is a microbubble generating device, generally indicated at 1, for the generation of microbubbles.

In brief, the device 1 comprises a gas supply conduit 2, a pair of liquid supply conduits 3, 4, a contact chamber 5, an orifice 6 and a nozzle 7. The flow directions through and along the respective conduits 2, 3, 4 and nozzle 7 are indicated by the arrows A, B, C, D. As will be explained below, D indicates the principal bubble flow direction along a principal longitudinal axis LX of the nozzle 7.

In a first embodiment, gas passes along gas supply conduit 2 to the contact chamber 5 whereupon the gas front 2a is contacted by impinging liquid delivered via the liquid delivery conduits 3, 4. As the gas and liquid is forced through the orifice 6 microbubbles are generated at the orifice 6 and just within the nozzle 7.

The gas and liquid supply conduits 2, 3, 4 are usually rectangular, though other shapes and configurations are perfectly possible. A typical height for the components 2, 3, 4, 5 is 10 to 60 μm, say 15 to 40 μm. Typical widths may be from 10 to 50 μm for the gas supply conduit 2, say 25 to 45 μm and 20 to 80 μm, say 30 to 70 μm for the liquid supply conduits 3, 4. The orifice typically has a width of 1 to 20 μm, say 2 to 18 μm, for example 5 to 15 μm.

The nozzle 7 is conical is shape in the specific embodiment shown, thereby providing three dimensional expanding geometry in the bubble flow direction D. In a preferred embodiment the nozzle 7 has a length of 300 to 400 μm and expands from a height equivalent to that of the orifice 6 to about 300 μm at its widest.

At the orifice 6 a continuous stream of gas encased in liquid is forced into the nozzle 7. As the gas is forced into the nozzle 7 shear forces cause the leading portion of the gas flow to break from the steam and generate a bubble of gas surrounded by liquid. Because of the expanding geometry of the nozzle 7 a velocity gradient is generated in the flow direction D which prevents the succeeding bubbles from colliding with the preceding bubbles, thereby limiting bubble coalescence and ensuring a mono disperse bubble population. It is postulated that the provision of three dimensional expanding geometry provides a further degree of freedom of bubble movement downstream of the orifice 6, thereby further reducing the likelihood of bubble collision over, say, two dimensional expanding geometries. For the avoidance of doubt, by 'three dimensional expanding geometry' it is meant a nozzle which expands in both a height and width dimension as distance along the length dimension increases.

In a preferred embodiment, the orifice 6 and nozzle 7 sizes and geometries will be chosen to ensure that a mono-disperse (or close to mono-disperse) bubble population is generated with diameters in the range of, say, 1 to 10 μm, with a population of from $10^8$ to $10^{10}$ bubbles/mL. In a particularly preferred embodiment the microbubbles have a dispersity index is less than 100%, preferably 50% or less and most preferably 35% or less.

Figure 4:
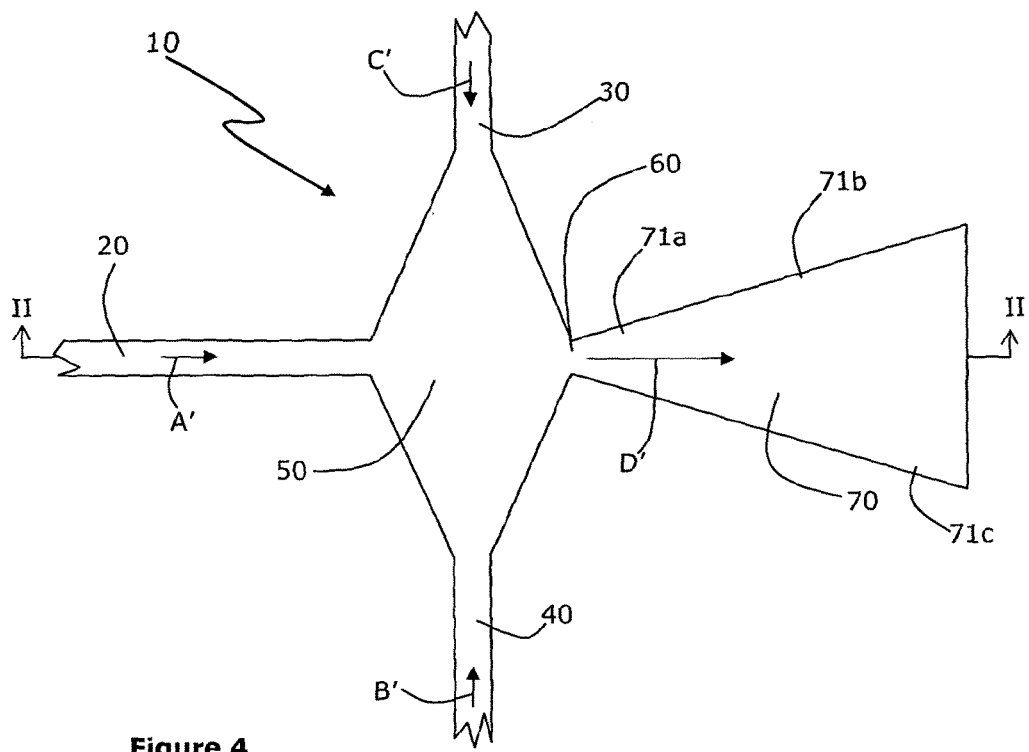
FIG. 4 shows a plan view of a second embodiment of the invention.
Figure 5:
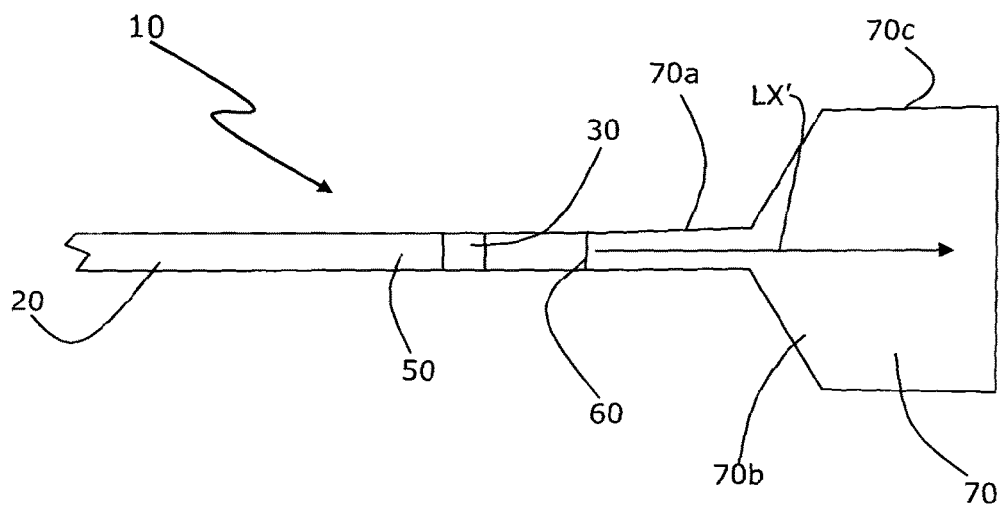
FIG. 5 is a sectional view of FIG. 4 along the line II-II.

Referring now to FIGS. 4 and 5, there is shown a further embodiment of nozzle geometry. A device 10 comprises a gas delivery conduit 20, a pair of liquid delivery conduits 30, 40, a contact chamber 50, an orifice 60 and a nozzle 70. The flow directions through and along the respective conduits 20, 30, 40 and nozzle 70 are indicated by the arrows A', B', C', D'. As will be explained below, D' indicates the principal bubble flow direction along a principal longitudinal axis LX' of the nozzle 70.

As before, gas passes along gas supply conduit 20 to the contact chamber 50 whereupon a gas front is contacted by impinging liquid delivered via the liquid delivery conduits 30, 40. As the gas and liquid is forced through the orifice 60 microbubbles are generated at the orifice 60 and just within the nozzle 70.

The supply conduits 20, 30, 40 and contact chamber 50 may have the same dimensions as discussed above in relation to the first embodiment.

The nozzle 70, however, has a complex shape which in plan (see FIG. 4) is triangular but in elevation (see FIG. 5) has a stepped profile.

It is convenient to consider the nozzle 70 in more detail. Immediately downstream of the nozzle 60 is, in plan, a triangular section 70a having divergent sidewalls 71a but with a base wall 72a and top wall 73a being at a constant height $h_1$. Downstream of the triangular section 70a is an inclined section 70b with divergent side walls 71b but with a base wall 72b and top wall 73b which are inclined to one another such that the distance between the two increases in the principal axial direction LX' of the nozzle 70. Downstream of the inclined section 70b is a terminal section 70c, again with inclined side walls 71c but with a base wall 72c and top wall 73c being at a constant height $h_2$. In one embodiment $h_1$ is from 10 to 60 μm, e.g. 25 μm and $h_2$ is from 20 to 120 μm, e.g. 50 μm.

As will be appreciated, the nozzle 70 has a first two dimensional expanding geometry in zone 70a, a three dimensional expanding geometry in zone 70b, and a terminal two dimensional expanding geometry in zone 70c. It is believed that this leads to distinct velocity gradients along the principal axis LX' of the nozzle 70 and helps to ensure a separation of generated bubbles to prevent collisions and to enable generation of a mono-disperse (or substantially mono-disperse) bubble population, with a concentration in the range of $10^8$ to $10^{10}$ bubbles/mL.

This 'step-wise' profile may be provided at more than one axial location within the nozzle 70. Moreover, the location of the (or the first) 'step' may be closer to or further from the orifice 60. The angle of incline of the divergent side walls 71b may be greater (e.g. up to 90° to the principal axis of the nozzle 70) or smaller than as shown. Accordingly, by 'stepped' or 'step-wise' it is meant that the angle of the walls changes along the length of the wall, rather than remaining substantially constant.

Other profiles of nozzle 7, 70 may be provided which increase in both a height and width dimension in the direction of bubble flow. For example, a nozzle with a plurality of steps or with a constantly increasing portion (e.g. conical) and a stepped portion. The cross-section of the nozzle in the three dimensional expanding region need not be circular, for example the cross section may be ovoid, or square or triangular (providing a square or triangular frusto-pyramid) or other regular or irregular expanding shape.

The liquid flowing through the liquid supply conduits 3, 4; 30, 40 is likely to comprise a lipid or blend of lipids. The lipids can be phospholipids and/or a lipopolymer emulsifier in an aqueous medium. Many known lipids or emulsifiers can be used.

The apparatus 1, 10 is useful in the manufacture of microbubbles which are useful as contrasting agents in ultrasound diagnostics. Furthermore the apparatus is also useful in the manufacture of microbubbles that can be used for therapy or diagnostics, e.g. the microbubble may be provided with an active ingredient, as will be described further below.

Figure 7:
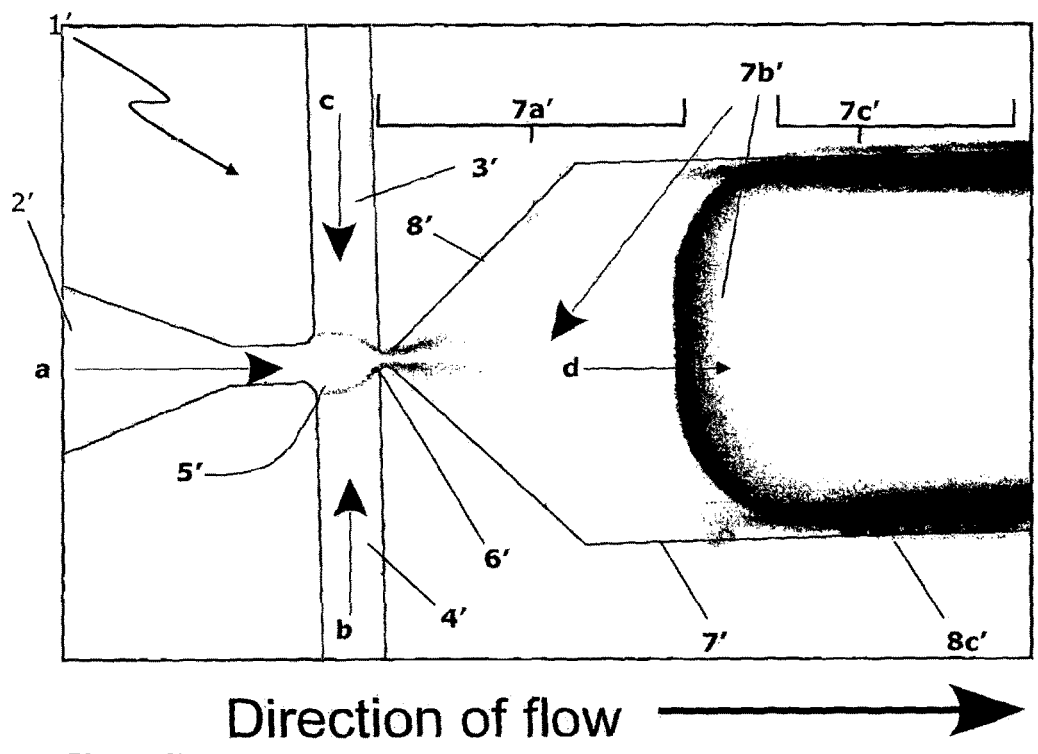
FIG. 7 shows a plan view of a third embodiment of the invention.

Turning now to FIG. 7, there is provided a third embodiment of bubble generation apparatus 1'. This embodiment is of similar form to that of FIG. 1 and so like components are similarly numbered but indicated with a prime (').

In brief, the device 1' comprises a gas delivery conduit 2', a pair of liquid delivery conduits 3', 4', a contact chamber 5', an orifice 6' and a nozzle 7'. The flow directions through and along the respective conduits 2', 3', 4' and nozzle 7' are indicated by the arrows a, b, c, d. As before, d indicates the principal bubble flow direction along a principal longitudinal axis of the nozzle 7'.

Here the nozzle 7' comprises a first section 7a' and a second section 7c', a third section 7b' comprising a step provided between the first and second sections 7a', 7c'.

The first section 7a' of the nozzle 7' comprises a triangular section in which divergent side walls 8' extend from the orifice 6'. At a turning point the divergent walls 8 become parallel to one another to provide a rectangular section. The base and top walls of this section 7a' do not diverge, thus the cross section at any point in the direction d from the orifice 6' to the end of the first section 7a' is rectangular.

In the second section 7c' the distance between the base and top walls has been increased in relation to that of the first section 7a'. The cross sectional profile of this section 7c' at any point in a direction d may be rectangular (including square), circular, ovoid or other shape. The top and base walls may diverge or may be parallel, the side walls may diverge or may be parallel. In the embodiment shown, the side walls 8c' are parallel as are the top and bottom walls.

In the third section 7b' the nozzle 7' is stepped to accommodate the difference in height between the first 7a' and second 7b' sections The contact chamber need not be the shape shown in the attached drawings. Other designs may be used.

The method of the invention can be used to produce a monodisperse microbubble population in a clinically appropriate timeframe. In some circumstances, one or other of production rate or monodispersity may be compromised to provide an appropriate population according to specific need.

As will be recognised, the above devices are preferably for use in a microfluidic chip. As such, the various components are etched, for example mechanically or chemically etched onto or into the chip.

FURTHER EXPERIMENTAL WORK

Using the apparatus described above and modified versions thereof, a number of experiments have been performed which demonstrate their utility and the properties of the microbubbles created using the device.

Introduction

Lipid and polymer stabilised microbubbles (MBs) have been used as contrast enhancers in ultrasound (US) imaging for nearly 30 years. The air-liquid interface and the compressibility of the MBs reflects and scatters sound waves more effectively than tissue interfaces alone, enhancing US images of internal organs.[1,2] MBs also show promise for therapeutic delivery, such as for the delivery of drugs for chemotherapy or DNA/siRNA vectors for gene therapy.[3-6]

Conventionally, MB emulsions are made from the sonication or the mechanical agitation of a mixture of lipids suspended in a solution in a vial, the head-space of which contains a low solubility gas required for the bubble core. Such physical agitation creates microbubble populations with a mean diameter of between 1-5 μm and a concentration of approximately $10^9$ to $10^{10}$ bubbles per mL.[4,6] It is clinically important that MBs should not exceed 8 μm in diameter, bubbles larger than this can cause complications in the blood stream such as arterial embolisms.[7] However, these techniques produce highly polydisperse MBs with a fraction of the populations having diameters as large as 10 or even 20 μm.[6] Further, the current commercial methods for MB generation only produce a basic, PEG/lipid-stabilised microbubble without a therapeutic payload. The handling and processing of MBs, once produced, is difficult without adversely affecting the bubble population. Microfluidics however, offers new routes for MB production and functionalisation with improved control over the bubble size distribution, ease of processing, and reduced volumes resulting in more effective use of costly or toxic materials. Commonly, MB production in microfluidics is achieved using a flow-focus geometry in which a liquid/lipid flow 'pinches' a gas phase inside a small aperture or orifice, which leads to a nozzle. The velocity gradient through the orifice followed by the resultant pressure drop causes the formation of bubbles that are 'pinched-off' in the orifice.[8,9] Early studies produced bubbles between 5 and 500 μm in diameter. Since then, much work has been done to refine the size and reduce the dispersity index of the MB populations generated in microfluidic devices.[19-15] Longo, Lee and Dayton[16-21] have used PDMS flow-focussing to produce monodisperse lipid coated MBs, with perfluorocarbon interiors, in the size range of 1 to 5 μm with excellent control over their dispersity, between 2 and 5 respectively. In a variation of this approach, Kumacheva et al. have used a similar approach but formed a gas core consisting of $CO_2$ plus a small amount of an insoluble gas such as argon. The MBs generated in the device had initial bubble diameters of around 30 μm but subsequently shrank to approximately 8 μm as the $CO_2$ dissolved into the surrounding aqueous phase leaving bubbles containing the insoluble gas.[22,23]

Seo et al. have also recently demonstrated a flow-focussing device that produced MBs in the range 3-9 μm in diameter, with a size variation of <5%.[24] Further, they demonstrated that the bubbles could be coated, via a three-step protocol, with a range of silica-coated nanoparticles to permit enhanced imaging via fluorescence and in principle magnetic resonance imaging (MRI). Examples of such multi-functional MBs include surface modification with quantum dots (QDs),[25] silica,[24] $Fe_3O_4$[25,26] and gold nanoparticles[24]. Other groups have investigated incorporating an organic layer inside the MB in order to load them with nanoparticles or hydrophobic therapeutic agents.[27-29] While the above approaches demonstrate the control in size distribution and versatility microfluidics can offer in terms of MB architecture, they are often time consuming and suffer from low MB concentrations (which fall short of that required for clinical application). Jiang et al. reported a multiplexed microfluidic device for mass bubble production with up to eight flow-focussing units, however this still only produced bubbles at the $10^5$ bubbles $mL^{-1}$ concentration range, four orders of magnitude lower than what is required for clinical use.[30] In addition, such methodologies often require careful adjustment of liquid viscosities and balancing of gas and liquid pressures inside the chip. The isolation of MBs after leaving the microfluidic device is often difficult at such low concentrations, and bubble images are commonly taken with high frame rate cameras in the outlet immediately following bubble formation rather than from isolated post-formation bubble populations.

In the following text, we demonstrate a new MB production regime that generates MBs, of suitable size, and at clinically relevant concentrations. The MB platform is very robust and reproducibility across multiple users, on multiple instruments, is high. Further, the use of multiplexed chips allowed a significant reduction in the time taken to prepare MB samples, to ~10 minutes for concentration of $10^{10}$ MB mL$^{-1}$. Finally, we demonstrate the single step assembly of complex bubble architectures for theragnostic purposes (FIG. 8) in which MBs were coated with liposomes containing either QDs, or fluorescein, via a biotin-streptavidin linkage. This technique is readily applicable to many other particle types. FIG. 8 shows a microbubble 10 comprising a gas core 11, surrounded by a lipid shell comprising lipids having a hydrophilic head 12 and a hydrophobic tail 14. Attached to the shell are biotin-streptavidin linkages 16 comprising streptavidin moieties 17 and biotin moieties 18. The biotin-streptavidin linkages 16 couple targeting antibodies 20 and liposomes 22 to the microbubble 10. The liposomes 22 comprise a payload 24, which can be a drug, marker or the like.

Materials and Methods

Materials

Microbubbles were prepared from a mixture of lipids (19.5 µL DPPC 20 mg mL$^{-1}$ and 6.5 µL DSPE-PEG2000 25 mg mL$^{-1}$) purchased from Avanti Polar Lipids (Alabaster, Ala., USA). All lipids were dissolved in chloroform, dried on the wall of a glass vial under nitrogen for 40 minutes and then re-suspended in a solution of 1% glycerine (Sigma-Aldrich, St. Louis, Mo., USA) and 4 mg mL$^{-1}$ NaCl. The vial was then vortexed for 1 minute and placed in a heated ultrasonic bath for 1 hour to facilitate the re-suspension of the lipid mix. Lipid solutions were then allowed to cool at 4° C. for 10 minutes prior to use in the microfluidic device. Other lipids would be suitable for use in the present invention, and suitable lipids would be apparent to the person skilled in the art, and their suitability and optimum conditions for use could be determined experimentally with no difficulties.

The aqueous synthesis of core-shell CdTe/CdS/ZnS quantum dots (QDs) was achieved by first preparing CdTe core QDs using methods described elsewhere.[31,32] Sequential shell growth of CdS followed by ZnS was achieved using the methods of Li et al. resulting in the synthesis of thioglycolic acid modified CdTe/CdS/ZnS QDs dispersed in water with an emission maxima at 615 nm.[33] The QDs were cleaned by adding two parts isopropanol to one part QD solution followed by centrifugation at 8000 rpm for five minutes. The supernatant was decanted and the QDs were re-dispersed in PBS buffer (pH 7.4, Gibco Life Technologies Limited, Scotland) by sonication to give a final QD concentration of 3 µM. Liposomes were prepared by mixing 1,2-Distearoyl-sn-glycero-3-phosphocholine (DSPC), Cholesterol, and 1,2-distearoyl-sn-glycero-3-phosphoethanolamine-N-[biotinyl (polyethyleneglycol)-2000] (ammonium salt) (DSPE-B-PEG2000), purchased from Avanti polar lipid (Albaster, Ala., USA). All dissolved in 50/50 Chloroform/methanol in a 63:32:5 molar ratio. After evaporating chloroform and methanol, the lipid film was rehydrated with PBS buffer containing either 0.5 mM Fluorescein (Ex. 492 nm Em. 517 nm, Sigma Aldrich, UK) or 3 µM CdTe/CdS/ZnS QDs (Em. 615 nm) to obtain liposomal solution with a final lipid concentration of 24 mg/ml. The liposomal solution was then extruded by mini extruder (Avanti polar lipids, Albaster, Ala., USA) through a 400 nm filter followed by 200 nm filter at 60° C. for final sizing. After extrusion, liposomes were then separated from the excess non-encapsulated fluorescein or QDs by passing through a Sephadex G-25 column (GE Healthcare, UK). It will be apparent that other labelling or active particles could be used in the present invention, provided they are compatible with microbubbles. Furthermore linker systems other than biotin/avidin could be used, again provided that they are generally compatible with microbubbles. Suitable particles and/or linkers would be apparent to the person skilled in the art, and their suitability and optimum conditions for use could be determined experimentally with no difficulties.

Microfluidic Design and Microbubble Generation

The microfluidic devices were fabricated by Epigem Ltd (Redcar, UK) in polycarbonate and SU-8 (a well-known epoxy-based negative photoresist)—other materials could of course be used. The design had an inlet channel for the gas and two opposing inlet channels for the introduction of the liquid phase. The flow was focussed through an orifice beyond which there was a single exit channel (FIG. 9a). The width of the liquid inlets was 50 µm and the gas inlet 30 µm. The width of the exit channel (nozzle) was 270 µm and chips were fabricated to a depth of 25 µm. In the case of the 3D expansion volumes, vide infra, an additional 25 µm or 50 µm depth was achieved by introducing additional photolithography in the lid of the microchip. The dimensions of the various channels are shown schematically in FIG. 11. Multiplexed chips were fabricated in the same way, but the design featured multiple bubble making modules on a single chip with a single inlet feeding in splitting evenly among the modules (FIG. 9b). As seen in FIGS. 9a and 9b the device comprises mounting holes 30, liquid inlets 32, gas inlet 34, bubble generation area 36 and outlet 38.

The chips were mounted in a custom-built holder 42 on the moveable stage of an inverted light microscope 44 (Eclipse Ti-U, Nikon, Japan). The chip holder 42 consisted of a recess into which the microchip 40 fitted closely. A manifold 45, which contained PTFE tubes (Supelco Analytical, USA) for liquid and gas lines was brought into firm contact with the chip 40 using a lever clamping arm. In the closed position a gas tight seal between the manifold 45 and chip 40 was formed, even under high pressure conditions (>40 psi). Flow of the liquid phase to the microchip 40 was delivered via a syringe pump 54 (Aladdin, World Precision Instruments, USA) and the gas flow from a pressurised cylinder 52 was regulated by a digital gas flow controller 50 (Alicat Scientific, USA). Both the syringe pump 54 and the gas flow controller 50 were controlled via a PC. The microbubbles were collected in a vial 46. A schematic of the instrument set-up is shown in FIG. 9c.

Microbubbles were generated by pumping the aqueous lipid solution through opposing inlets and a gas flow through the remaining central inlet. Liquid flow rates were varied between 20-50 µL mL$^{-1}$ and gas pressure between 10-40 psi. A small delay, of a few seconds, was implemented before starting the MB collection to ensure flow rates and gas pressures had reached their desired rate. Samples were analysed by injecting 30 µL of the MB solution, taken from the centre of the vial 46 so the sample was homogenous and there were no pre-concentration effects from the intrinsic buoyancy of the MBs, into a 50 µm deep observation cell and imaged using optical microscopy. All microbubble images were obtained with a 60× objective.

Ultrasound Attenuation and Scatter Measurements

The acoustic scattering and attenuation properties of MBs generated by both microfluidic and mechanical agitation methods (3M ESPE CapMix, 3M UK PLC, Bracknell, UK) were measured. A 25 mm diameter cylindrical chamber containing the MB suspension, at an approximate concentration of $2\times10^6$ MBs mL$^{-1}$, was immersed in a larger tank containing de-gassed 20° C. water and mixed using a magnetic stirrer. The chamber had three acoustically transparent windows, to either measure acoustic signals transmitted through or scattered at 90°. A 5 MHz single element weakly focused ultrasound transducer (V310, Olympus-NDT, Waltham, Mass. USA) was used to excite the MB population. The transducer was situated approximately 20 mm from an acoustic window outside the chamber and a 1 mm needle hydrophone (Precision Acoustics, Dorchester, UK) was either placed in front of an acoustic window, parallel or perpendicular to the ultrasound transducer for either attenuation or scatter measurements, respectively. Ultrasound excitation waveforms were designed in MatLab (Mathworks, Natick, Mass., USA) and loaded into an arbitrary waveform generator (33250A, Agilent Technologies, Santa Clara, Calif., USA), which were then amplified by a 55 dB power amplifier (A150, E&I, Rochester, N.Y., USA) and used to drive the ultrasound transducer. A 10 µs duration pulse with a bandwidth of 3-8 MHz and a root mean square pressure ($P_{rms}$) of 60 kPa was used to measure the attenuation as a function of frequency for both MB populations. Scattering from these two MB populations generated by a 4 MHz tone burst over a $P_{rms}$=25-250 kPa range were also measured using the hydrophone, but with the addition of a 40 dB preamplifier (5072, Olympus-NDT, Waltham, Mass. USA). All received signals were digitized and stored using a LeCroy oscilloscope (WaveRunner 44Xi, LeCroy Corporation, Chestnut Ridge, N.Y., USA) operated in sequence mode. Each measurement consisted of 200 individual excitations at a given excitation frequency and pressure, which were then processed and averaged in MatLab. The MB shell stiffness ($S_p$) and friction ($S_f$) for these two populations were estimated by comparing the measured attenuation coefficient with a theoretically predicted coefficient using a technique demonstrated most recently by Faez et al.[34]

On-Chip Surface Modification of Microbubbles

For experiments involving the attachment of liposomes to MBs, the liposome dispersion was incubated with 0.6 µM neutravidin (Life-technologies limited, UK) for 15 minutes with agitation to allow proper mixing. The lipid solution for the generation of MBs was then added to the liposome-neutravidin mix and allowed to incubate at 4° C. for a further 15 minutes. The mixture was then introduced into the microfluidic device through the lipid stream.

Imaging and Data Analysis

The microchip was mounted on a custom made microscope stage mounted on an inverted microscope. Images of the microbubble formation inside the microfluidic device and of bubble populations were observed using 15× and 60× objectives respectively. A CCD camera (DS-Fi1 SMega pixel, Nikon, Japan) and Nikon Elements Software-D (Version 3.2) were used for capturing images. For bubble images requiring fluorescence, images were taken on an upright fluorescence microscope with a 100× oil emersion objective (Nikon, Japan) equipped with an Orca II CCD camera (Hamamatsu Photonics K.K. Japan). Images were analysed using ImageJ freeware (http://rsbweb.nih.gov/ij/) and statistically analysed using Origin Pro (Version 8.5).

Results

Microbubble Formation—Single Bubble Regime

FIG. 10 shows two microbubble forming regimes in the flow-focussing device. FIG. 10a shows a conventional approach to forming monodisperse MBs in which the bubbles are 'pinched off' in the orifice and a narrow stream of individual bubbles exit via the outlet channel (i.e. the nozzle). FIG. 10b shows the bubble-forming regime of the present invention in which the bubbles are formed outside and downstream from the nozzle and are seen to occupy most of the outlet area.

In the monodisperse regime MB formation was achieved by varying the gas pressure and lipid flow rates until equilibrium was established between the two phases just before the nozzle (gas pressure 5 psi, liquid flow rate between 10 and 45 µL min$^{-1}$). At this point, no bubbles were formed and the bulb of the gas was static. The gas pressure was then increased slightly so that the bulb extended towards the orifice and the lipid phase pinches the gas phase from two sides to produce a stream of individual bubbles. As expected the microbubble diameter, d, decreased monotonically with increasing liquid flow rate, $Q_l$;[9,35]

$$d/D \alpha (Q_g/Q_l)^{\hat{}}n$$

where D is the orifice diameter. The exponent, n, depends on the physical geometry of the device used to produce the bubbles. For instance, n varies between n=0.17 for axi-symmetric geometries[36] to n=0.37 for microfluidic flow-focusing devices with elongated nozzles.[11] The device used in this investigation had a planar flow-focussing design with a short nozzle and while n=−0.4 proposed by Garstecki et. al fits the data (FIG. 12, dashed line) we note that in our case n=−2 provides a better fit (black line). This departure from the previously found law possibly reflects that $Q_g$ is not fixed in our experiments leading to no MB formation for liquid flow rates less than 15 µL min$^{-1}$ or greater than 45 µL min$^{-1}$. The variation in microbubble size, the dispersity index described as (standard deviation of bubble size/mean bubble size)×100 also varied slightly with flow rate, increasing towards the extremes. For optimum flow rates in the middle of this range, where bubble formation was stable, the dispersity index was as low as 10%.

Microbubble Formation—Micro-Spray Regime

Whilst the results described above are suitable for the generation of MBs of controlled size, the concentration of MBs produced ($10^6$-$10^7$ MB mL$^{-1}$) is far too low for a clinically relevant concentration, where realistically $10^{10}$ MB mL$^{-1}$ needs to be achieved in a suitable time.

To improve the rate of MB production we have investigated a new formation regime in which the flow-focussed region of the gas bulb extended into and beyond the orifice toward a region of sudden pressure drop, FIG. 10b. This pressure drop was achieved by a combination of the widening of the exit channel, in the plane of the chip, as well as by an abrupt increase in the depth of the chip. The pressure drop in the outlet channel is integral to the formation in this regime and any backpressure due to flow resistance in the fluidic system caused a decrease in bubble concentration or the breakdown of bubble formation. To obtain this new bubble formation regime, a second layer of photolithography was introduced into the lid of the microfluidic device that doubled the depth of the outlet channel from 25 µm to 50 µm. This reduced the flow resistance in the outlet by a factor of 10, from $10^{13}$ kg m$^{-4}$ s$^{-1}$ to $10^{12}$ kg m$^{-4}$ s$^{-1}$ for the 25 µm and 50 µm deep outlets, respectively. In this new regime MBs were made at a frequency of $10^6$ bubbles s$^{-1}$, which gave a MB concentration of $10^8$ to $10^9$ bubbles mL$^{-1}$ without any pre-concentration.

Figure 13A:
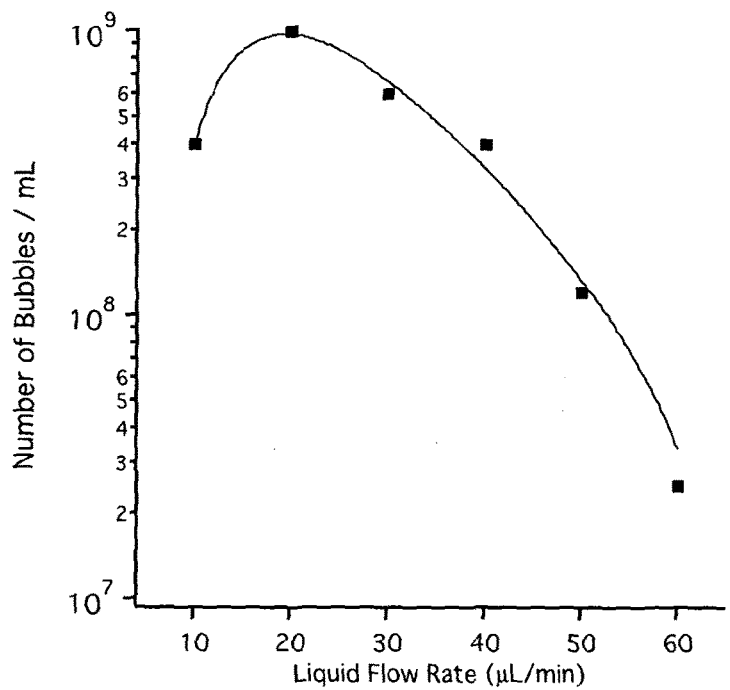
Figure 13B:
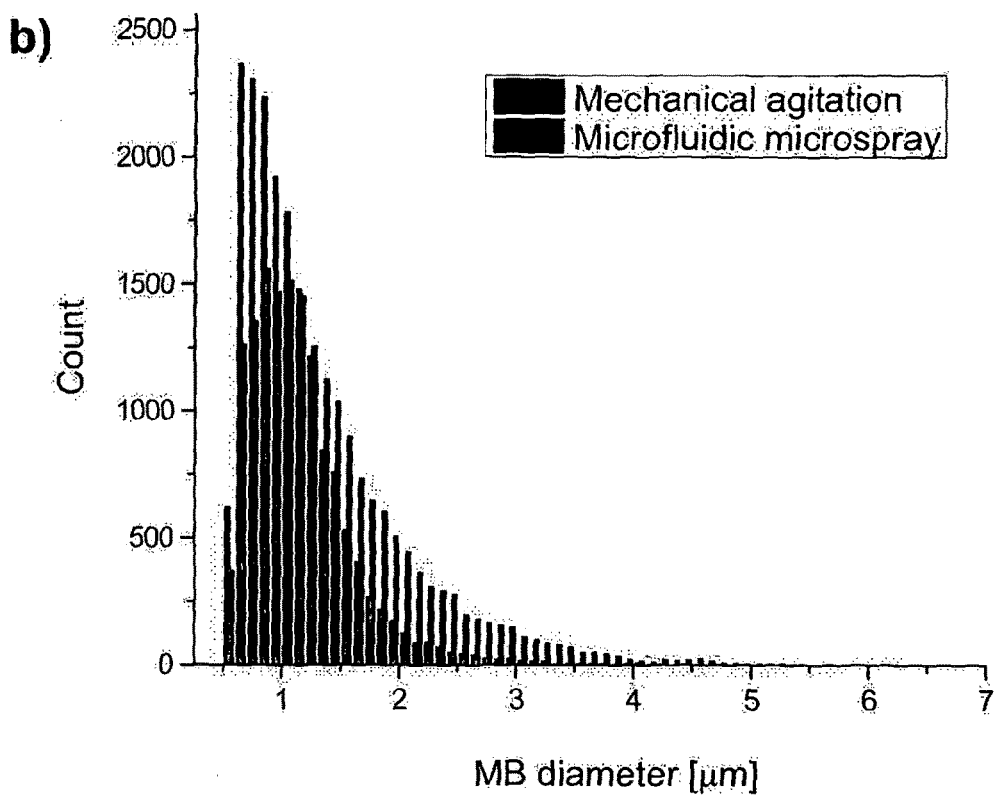

FIG. 13a shows a graph of flow rate versus MB concentration, obtained at a fixed gas pressure of 12.5 psi. The optimum flow rate that gave the maximum MB yields was 20 µL min$^{-1}$. As flow rate was increased, the concentration of MBs decreased due to an increase in fluid velocity focussing the gas stream into a narrower stream and moving it away from the sides of the nozzle where the MBs were generated. The size and variation of the MBs formed in this method was not as well-defined as MBs formed in the single bubble regime. FIG. 13b shows a sample of MBs generated by the device and a histogram taken from data from over 10,000 MBs (red histogram). The average microbubble size from the device was 1.4 µm and the dispersity index was approximately 50%. The shift in the distribution to slightly higher sizes (red histogram) compared to those obtained using a commercially available product formed by mechanical agitation (blue histogram) is in fact beneficial, as these MBs provide a greater scattering effect by an increased scattering volume. In addition, none of the MBs produced using the microfluidic micro-spray regime were greater than 6 µm in diameter whilst those prepared using mechanical agitation had MBs up to 8 µm in diameter, with a few bubbles greater than 20 µm (which were not included in the histogram). At a production rate of $10^6$ bubbles $s^{-1}$, it took just less than an hour to generate 1 mL of MBs (at ~$3\times10^9$ MB $mL^{-1}$). This was a considered too long to be practical and in order to decrease the time taken, several bubble maker modules were integrated onto a single device. The formation of MBs in each of the bubble modules behaved in an identical manner to a single module device and produced microbubble concentrations of $10^8$-$10^9$ bubbles $mL^{-1}$ in 10 minutes. In addition, in the event of one of the modules failing, such as a blockage, the remaining three modules would continue to produce the full milliliter of MBs.

The microfluidic devices were designed for generating MBs in a clinical environment, therefore the robustness and the reproducibility of the device was imperative. Three prototype MB generation instruments were constructed and tested in three different laboratories and by four different users. Table 1 shows the results of quality assurance testing. Users A-D used three separate machines to generate a sample of bubbles under the same conditions (with different chips). It is evident from Table 1 the bubble generation on a single machine, by a single user showed excellent repeatability and further there was only a slight variation between the different users.

TABLE 1

| | User A, Inst. 1 | User B, Inst. 1 | User C, Inst 2 | User D, Inst. 3 | Average |
|---|---|---|---|---|---|
| Mean diameter (µm) | 1.3 ± 0.08 | 1.3 ± 0.12 | 1.2 ± 0.06 | 1.1 ± .06 | 1.2 ± 0.08 |
| Mean concentration ($\times 10^8$ MB $mL^{-1}$) | 1.2 ± 0. | 1.9 ± 0.9 | 1.2 ± 0.3 | 1.8 ± 0.5 | 1.5 ± 0.4 |

Table 1—Results of Quality Assurance testing of the microfluidic instrument. Each user (A-D) completed the bubble production experiment three times and the mean values are presented in the table. Three separate but identical microfluidic systems were used for the testing and the bubble size, dispersity index and concentration were analysed.

The average mean microbubble sizes were between 1.1-1.4 µm which corresponds to a variation of between 1.6-8% Relative Standard Deviation (RSD).

The repeatability of the average size of the MBs produced under the same operation conditions was excellent, with only a 4% variation in size across users and instruments. The concentration of the MBs showed good repeatability, between $9.4\times10^7$ and $3.0\times10^8$ MB $mL^{-1}$, with a maximum of 25% variation in concentration between the four users and three machines. The instrument requires minimal user interaction and was operated simply by clipping the chip into the stage and clamping the manifold in place, and adjust flow rates and gas pressure to pre-set values. Since this multi-user test we have found that it is possible to obtain a 10 fold increase in MB concentration, in the same time, under the same conditions of pressure and flow rate by increasing the lipid concentration from 0.5 mg/ml to 3 mg $mL^{-1}$ in the liquid stream. Thus resulting in $10^9$-$10^{10}$ MB $mL^{-1}$ being produced within 10 minutes in the multiplexed chips.

Ultra-Sound Characterisation of Microfluidic Microbubbles

Figure 6:
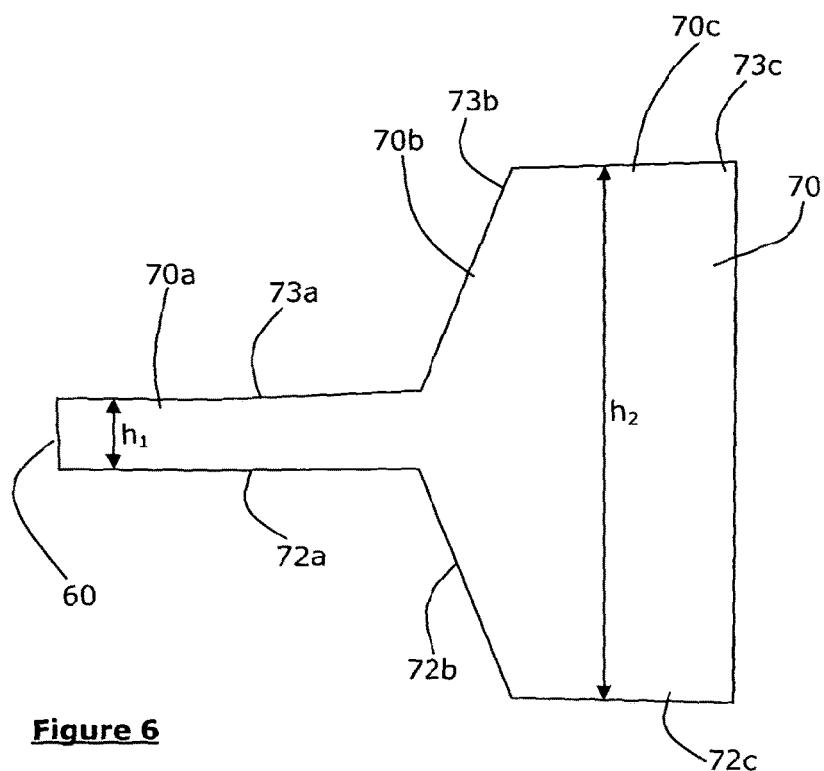
FIG. 6 is a detail of FIG. 5.

The ultrasound (US) characteristics of the MBs generated in the microfluidic spray regime were compared to those of commercially available MBs. FIG. 14a shows the averaged attenuation per centimeter over a frequency range of 3-8 MHz for both microfluidic and shaking generated MBs. The microfluidic MBs have slightly higher ultrasound attenuation over this frequency band, which suggests a greater interaction with the ultrasound field. The mean shell parameters were estimated as shell stiffness, $S_p=0.76\pm0.03$ N/m and shell friction, $S_f=0.30\pm0.02$ 10-6 kg/s for the shaking method and $S_p=0.72\pm0.03$ N/m and $S_f=0.32\pm0.02$ 10-6 kg/s for the microfluidic method.[34] FIG. 6b shows an example of the spectrum for scattering for excitation at 4 MHz with a $P_{rms}=250$ kPa US pulse. Scatter from the microfluidic MBs was approximately twice that of that detected from the MBs generated by mechanical agitation. Further, for both populations sub-harmonic, ultra-harmonic and super-harmonic emissions were observed with the microfluidic MBs demonstrating enhancement of the sub-harmonic and super-harmonics. One possible explanation for this would be if MBs produced by the shaking method contained a larger percentage of multilayer coatings. Some evidence that this might be the case has come from comparison of Force-spectroscopy experiments undertaken on MBs produced by the shaking method[37,38] with those produced by microfluidics.[39]

Single-Step Formation of Liposome Functionalised MBs

Liposomes, containing QDs or fluorescein, were attached to the MB surface using neutravidin—biotin linker chemistry, as shown schematically in FIG. 8. The coatings were achieved using the same microfluidic chips as used to generate plain MBs. Neutravidin functionalised liposomes, containing with QDs or fluorescein, were mixed with the lipid solution used to make MBs prior to introduction into the microchip. The only difference in the lipids used to coat the MBs was that the PEG lipid used to stabilise the MBs was replaced with a biotin displaying variant.

FIG. 15b shows MBs coated with liposomes containing QDs, which was seen as the red fluorescence outlining the bubbles and 17c shows a histogram of the microbubble size.

The attachment of liposomes typically led to an increase in MB concentration to ~$3.5\times10^9$ bubbles $mL^{-1}$ as well as slightly higher variation in the size distribution with some MBs as large as 9-10 µm in diameter being observed. However, when compared to commercially available microbubble contrast agents, the maximum bubble diameter is still much smaller for the microfluidic bubbles. FIG. 15b shows that the functionalised MBs were clearly formed with the liposomes containing QDs coating the outside to the bubble surface, indicating the successful self-assembly of the microbubble lipids, with the neutravidin acting as a cross-linker between the MBs and the liposomes. Close observation of the MBs showed an even and complete coverage of the liposomes around the edge of the bubble image, suggesting maximum loading of the liposomes to the bubble surface. In another example, liposomes encapsulating fluorescein were loaded onto the surface of the MBs in a single microfluidic operation. Notably, from the image in FIG. 15b, the lack of background fluorescence suggests a good uptake of the liposomes onto the MB surface with minimal amount of liposomes remaining in solution. The bubbles did not require any additional incubation time or post-procedure washing steps, thus dramatically reducing the long procedural times usually associated with conventional batch methods of functionalised MB preparation.

In addition, the lifetime of the functionalised MBs, an important parameter for clinical US agents, was also investigated. FIG. 15d shows the lifetime of plain MBs versus MBs surface functionalised with liposomes at room temperature. The functionalised MBs showed a higher initial concentration than the plain MBs and over a period of 3 hours, the functionalised MBs only showed a 37% reduction in concentration from the initial count compared to the plain MBs that showed a 95% reduction in concentration. Presumably this occurs due to the additional liposome layer providing an increase in the resistance to gas permeation. In these experiments, both the QDs and the fluorescein were model examples that could later be replaced with chemotherapy drugs or gene therapy agents and added to the surface of the MBs in a simple, single-step operation. Also, it will be appreciated that this methodology could be readily adapted to attach many other types of particles.

CONCLUSIONS

We have demonstrated a microfluidic approach to the generation of multi-functional MBs for combined US and therapeutic applications—this approach has been termed microspray, which differentiates it from prior art microfluidics techniques where individual bubbles are pinched off. The microfluidic devices use a 3D expanding geometry to create a new regime for MB production capable of producing $10^8$-$10^9$ MBs mL$^{-1}$ range or higher. The chips were tested by a range of users in three different locations and demonstrated excellent reproducibility. Multiplexing the chips has reduced generation time to 10 minutes and in addition we have demonstrated the surface modification of the MBs with liposomes containing QDs and fluorescein in a single operation in a simple microfluidic device with improved concentrations and bubble lifetimes. Further, we have also found that increasing the lipid concentration, for the MB shell, by a factor of 3 leads to a 10 fold increase in the MB concentration, indicating that this route is capable of producing clinically relevant populations of $10^{10}$ MB mL$^{-1}$ in ~10 minutes.

Linker Systems

As discussed above, the present invention is well suited to use with a number of linker technologies to allow the attachment of moieties to the shell of the microbubbles. A biotin/avidin system is described in detail, and this is a well-known and widely used linker system. However, there are many other systems which may be suitable. Klibanov 2009 (Med Biol Eng Comput (2009) 47:875-882) and Klibanov 2005 (Bioconjugate Chem. 2005, 16, 9-17), for example, explain some suitable linker systems.

Linker systems known in the art in respect of microbubbles include:
DNA
Maleimide (on PEG):dithiopyridine (on PEG)
Maleimide (on PEG):thiol (on PEG)

FIG. 17 shows a number of 'short spacer' cholesterol-based amphiphilic linker molecules suitable for anchoring into the shell of microbubbles, along with an indication of commercial sources of such molecules and a brief description of each molecule. FIG. 18 shows a number of 'spacer-less' PE-based amphiphilic linker molecules (mostly DPPE derivatives) suitable for anchoring into the shell of microbubbles, along with a brief description of the molecule. It will be apparent that these linker molecules are suitable to activate or functionalise the shell of a microbubble for linkage to another moiety, e.g. a liposome, protein or the like.

A difference between directional versus non-directional coupling between linkers should be appreciated. This is illustrated in FIG. 16, with the top line representing directional linkage, and the three lines below representing non-directional linkage.

In terms of linkers for non-directional coupling, the biotin-avidin-biotin system is obviously a good example. Linkers based on the following chemistries would also be non-directional:
Maleimide-Dithiol-Maleimide
Amine-diacid-amine (NHS/EDC mediated amide formation)
Acid-diamine-acid (NHS/EDC mediated amide formation)
{Hydroxamic acid-di(nitrophenylester)-hydroxamic acid}
{Nitrophenol ester-dihydroxamic acid-nitrophenol ester}
N-hydroxysuccinimide-diamine or dithiol-N-hydroxysuccinimide
{Oligonucleotide-oligonucleotide-oligonucletide}
Cyanuryl chloride-diamine or dithiol-cyanuryl chloride
Dithiopyridine-dithiol-dithiopyridine In terms of linkers for directional coupling, linkers based on the following chemistries would be suitable:
Amine-acid
Hydroxamic acid-paranitrophenyl ester
Oligonucleotide-oligonucleotide
Thiol-maleimide
Thiol-dithiopyridine
Thiol or amine-N-hydroxysuccinimide
Amine-cyanuryl chloride Furthermore, the following are examples of chemical systems that are suitable for binding proteins to microbubbles:
1. Biotinylated lipids can be used to bind to avidin/streptavidin and (if they are available or can be made) via these to a biotinylated protein.
2. Nitrilotriacetic acid lipids can be used to bind His-tagged proteins (but the binding is not very strong).
3. Maleimide lipids can be used to bind any protein with a free SH grouping (*Bioconjugate Chem.*, 2007, 18, 101).
4. Dithiopyridine lipids can be used to bind any protein with a free SH grouping.
5. N-hydroxysuccinimide lipids can be used to bind any protein with a free $NH_2$.
6. paraNitrophenol ester lipids can be used to bind any protein with a free $NH_2$.

In either of cases 3 or 4, free $NH_2$ groups in the protein can be converted to free SH groups using Traut's reagent (*Bioconjugate Chem.*, 2007, 18, 101).

Thus, it can be seen that there are many systems (of which the above represent several suitable examples) that can be used to provide functionality to the surface of microbubbles and thereby link additional moieties to microbubbles. Further information regarding linkers can be found in *Soft Matter* 2010, 6, 6036; *Adv. Funct. Mater.*, 2007, 17, 1910; *Electrochim. Acta*, 2005, 50, 4248; *Angew. Chem. Int. Ed.*, 2004, 43 1265; *ChemPhysChem*, 2010, DOI:10.1002/cphc.200900798; *J. Am. Chem. Soc.*, 2000, 122, 6492; *J. Phys. Chem. A.*, 2007, 111, 12372; and *Biophys. J.*, 2009, 96, 1554

Experimental Work Relating to Addition of a Hydrophobic Phase to Microbubbles

Further work has been conducted to examine the addition of hydrophobic materials to the microbubbles. These hydrophobic materials were either added internally or external to the microbubbles. Adding a hydrophobic phase to the microbubbles increases the potential to use the microbubbles for the delivery and/or storage of hydrophobic materials such as drugs, dyes or the like.

Microbubbles Coated with Lipid-Coated Oil Nano-Droplets (LOND)

Microbubble architecture with Lipid coated Oil Nano-Droplets (LONDs) attached is essentially the same as the attachment of lipid vesicles (FIG. 19). A microbubble 60 comprises a shell 62 and a gas core 63. The shell comprises biotin moieties attached to the outside. Biotin-avidin-biotin linkages 65 link oil droplets 66 (which also have biotin moieties on their surface) to the shell 62 of the microbubble. The oil core 68 of the droplets can contain a drug or other hydrophobic component.

The LONDs are created using an oil. In the presently described work we used squalene, although we have used squalene and olive oil to date. However, it should be noted that any immiscible oil can be used, e.g. omega 3 oil, banana oil and peanut oil. Lipid (egg phosphatidyl choline—250 mg, 1% DOPE—cap biotinyl) is dissolved in 1 g of oil and mixed by a process of vortexing, sonication in a water bath and homogenisaton using a polytron 1300D. The volume is made up to 10 ml with phosphate buffered saline (or any other aqueous media) and then passed through a high pressure homegenisation system (Emulsflex C5, Avestin—Canada) at pressures between 10,000 and 30,000 psi. This creates oil droplets of narrow size distribution between approximately 200 and 100 nm (although actual size depends upon a number of factors including viscosity of oil, temperature etc). For the purpose of imaging, a fluorescent probe (fluorescein) was added into the oil prior to lipid addition and LOND formation.

Following LOND formation, neutravidin (or streptavidin) was added to enable binding of the LONDs to the bubble lipids. The 'activated' LONDs were added to the microbubble lipid mixture prior to introduction into the chip—as previously described for lipid vesicle loaded microbubble formation, and bubble formation proceeded at 14 psi, 30 µL/min in the micro-spray regime (FIG. 20), with the nozzle having expanding 3D geometry.

Figure 21A:
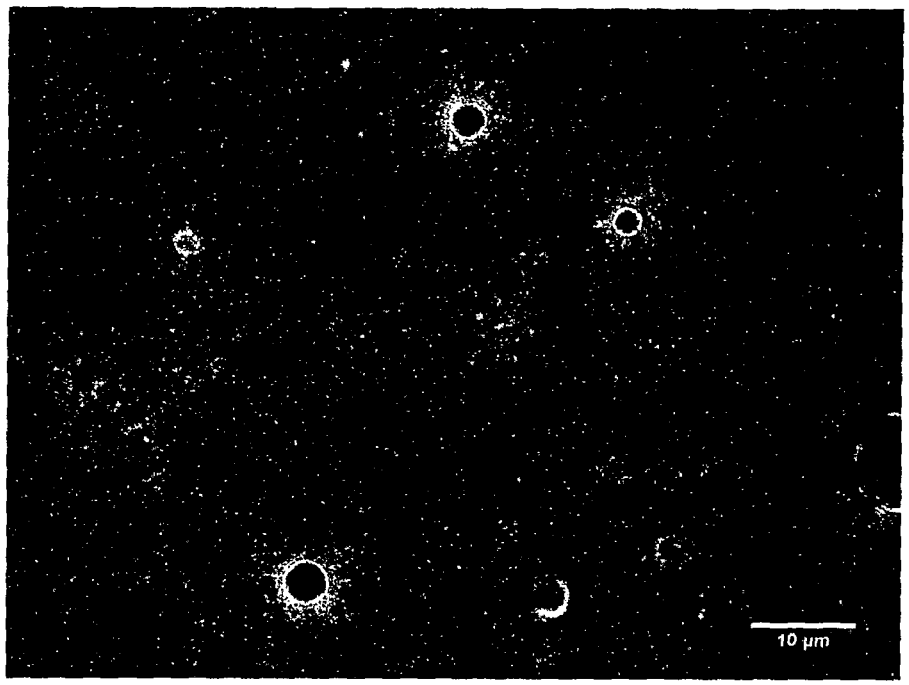
Figure 21B:
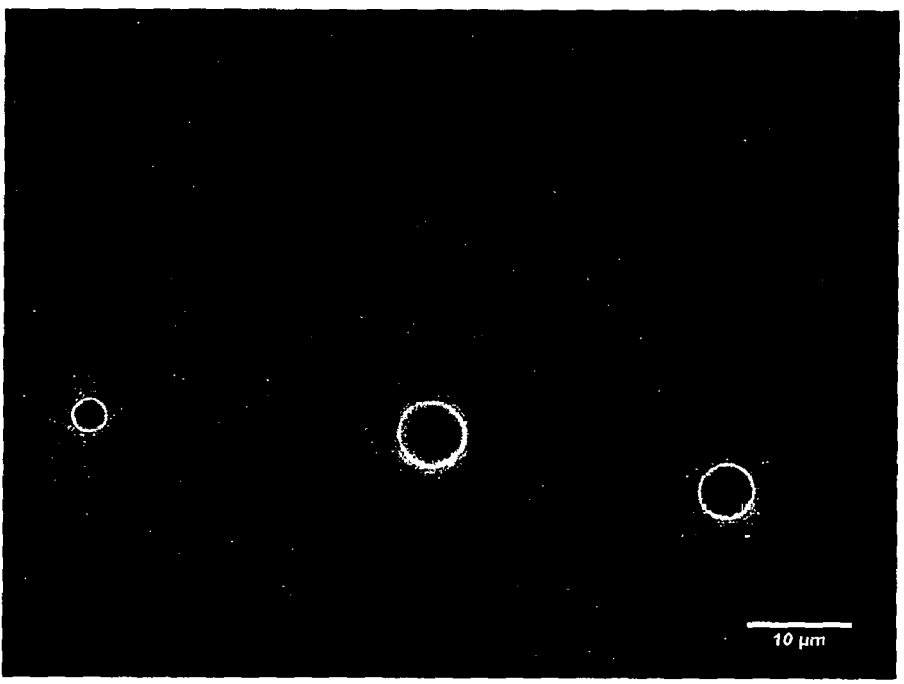

Images in FIGS. 21a and 21b show representative microbubbles with a 'halo' of green (fluorescence due to fluorescein in the oil) around their periphery.

Oil Layer Inside the Microbubble, e.g. for Delivery of Hydrophobic Drugs.

This work involved the additional of a thin oil layer on the inside of the microbubble in order to delivery hydrophobic drugs (FIG. 22). As can be seen, a microbubble contains a shell 80, with a layer of oil 82 within the shell, and a gas core 84. This involved a new chip design, with extra inlets to bring in the oil phase to the bubble production area. In fact two chips were designed which were named designs SP1 and SP2 (see FIG. 23).

The SP1 design allowed the oil phase (i.e. squalene) to meet the aqueous, lipid containing phase at a T-junction before introduction to the bubble formation area. Bubbles were formed when these combined laminar flow streams reached the nozzle area. In the SP2 design, the oil phase was introduced to the bubble forming area directly before the aqueous lipid phase, contacting the gas immediately prior to the aqueous lipid phase (FIG. 24).

Whilst the formation of oil in microbubbles is not a new concept in itself, previous microfluidic attempts have only used the conventional single bubble (i.e. non-microspray) regime. Although the schematic of FIG. 24 suggests that the microbubbles were generated in a conventional single bubble regime, in the present experiment microbubbles were specifically formed using a microspray regime, as shown in FIG. 25. However, the microchips did not feature the 3D expanding nozzle geometry at this stage. Bubbles were successfully generated, thus demonstrating the principle of the technique. However, with the addition of the 3D expanding geometry the bubble production would be greatly enhanced.

FIG. 26 shows images of the microbubbles formed by the micro-spray regime containing the oil layer. In these images the oil contains the fluorescent label fluorescein and can clearly be seen in the fluorescent images, indicating successful incorporation of the oil layer.

Examples of Suitable Materials for Microbubble Shells

As discussed above, there are a range of materials which can be used to form the shell of a microbubble. In general the most suitable materials are amphiphilic molecules or molecular complexes which are able to self-assemble into a membrane layer. Typically the materials are delivered to the microbubble forming system in an aqueous medium, but other media could be used.

A key group of compounds are lipids, which in the context of the present invention is used to refer to amphiphilic molecules comprising a hydrophobic hydrocarbon tail (or several tails) and a hydrophilic head.

Perhaps the most relevant lipids are phospholipids which typically consist of amphiphilic molecule typically with two, hydrocarbon, hydrophobic tails and a phosphor containing, hydrophobic, head group. A classic example of a phospholipid is 1-oleoyl-2-palmitoyl-sn-glycero-3-phosphocholine (POPC). The hydrocarbon tails can vary in length and the number of double bonds—they can also be asymmetric. There are several 'standard' head groups: PC—phosphatidylcholine; PS—phospatidylserine; PE—phosphatidylethanolamine; PG—phosphatidylglycerol; PA—phosphatidic acid. Various groups or polymers etc. can be added onto the head group of the phospholipids to form modified phospholipids, e.g. PEG (polyethylene glycol).

In the examples described above a mixture of dipalmitoylphosphatidylcholine (DPPC) and 1,2-Distearoyl-phosphatidylethanolamine (DSPE) PEG2000 (with or without biotin linked to the head group) was used, but numerous other mixtures of phospholipids have been used successfully as well.

Other materials can also be used to form the shell of the microbubbles:

"Proteins/Peptides"

Previous commercial microbubbles have used a coating of albumin, which in fact were the first generation of commercial microbubbles. Other known proteins which can be suitable include cerato ulmin and ranaspumin-2. In theory any protein which has a hydrophilic and a hydrophobic domain could be used to create the coating, provided that it could readily assemble into membrane. Peptides could be designed to specifically have hydrophilic and hydrophobic domains and self-assemble, which would allow mass production.

"Polymers"

Various polymers could be used to form the microbubble shell, for example block copolymers. A block copolymer is defined as a covalently bound polymer constructed from monomer blocks or sequences which can alternate between different monomers within the sequence—e.g. ABABABAB or AAABBBAAA (where A & B are different monomers). Block copolymers are classified based on the number of blocks they contain and how the blocks are arranged. Many di-block copolymers would be suitable for microbubble formation, provided they comprise at least a hydrophobic domain and a hydrophilic domain, but higher numbers of blocks may also be useful.

ACKNOWLEDGEMENT

FIGS. 1, 2 and 4 were adapted from Kanaka Hettiarachchi, Esra Talu, Marjorie L. Longo, Paul A. Dayton and Abraham P. Lee, Lab on a Chip, 2007, Issue 7, pages 463-468.

REFERENCES

1. M. J. K. Blomley, J. C. Cooke, E. C. Unger, M. J. Monaghan and D. O. Cosgrove, *British Medical Journal*, 2001, 322, 1222-1225.
2. E. Stride and N. Saffari, *Proceedings of the Institution of Mechanical Engineers Part H-Journal of Engineering in Medicine*, 2003, 217, 429-447.
3. S. Hernot and A. L. Klibanov, *Advanced Drug Delivery Reviews*, 2008, 60, 1153-1166.
4. S. Qin, C. F. Caskey and K. W. Ferrara, *Physics in Medicine and Biology*, 2009, 54, R27-R57.
5. K. W. Ferrara, M. A. Borden and H. Zhang, *Accounts of Chemical Research*, 2009, 42, 881-892.
6. Y. Liu, H. Miyoshi and M. Nakamura, *Journal of Colloid and Interface Science*, 2006, 114, 89-99.
7. S. Tinkov, C. Coester, S. Serba, N. Geis, H. Katus, G. Winter and R. Bekeredjian, *Journal of Controlled Release*, 2010, 148, 368-372.
8. P. Garstecki, I. Gitlin, W. DiLuzio, G. M. Whitesides, E. Kumacheva and H. A. Stone, *Applied Physics Letters*, 2004, 85, 2649-2651.
9. P. Garstecki, M. J. Fuerstman, H. A. Stone and G. M. Whitesides, *Lab on a Chip*, 2006, 6, 437-446.
10. M. Hashimoto, P. Garstecki and G. M. Whitesides, *Small*, 2007, 3, 1792-1802.
11. E. Castro-Hernandez, W. van Hoeve, D. Lohse and J. M. Gordillo, *Lab on a Chip*, 2011, 11, 2023-2029.
12. M. A. Herrada and A. M. Ganan-Calvo, *Physics of Fluids*, 2009, 21.
13. E. Stride and M. Edirisinghe, *Soft Matter*, 2008, 4, 2350-2359.
14. M. Hashimoto, S. S. Shevkoplyas, B. Zasonska, T. Szymborski, P. Garstecki and G. M. Whitesides, *Small*, 2008, 4, 1795-1805.
15. M. Hashimoto and G. M. Whitesides, *Small*, 2010, 6, 1051-1059.
16. Y. C. Tan, V. Cristini and A. P. Lee, *Sensors and Actuators B-Chemical*, 2006, 114, 350-356.
17. E. Talu, K. Hettiarachchi, H. Nguyen, A. P. Lee, R. L. Powell, M. L. Longo, P. A. Dayton and Ieee, in 2006 *Ieee Ultrasonics Symposium, Vols 1-5, Proceedings*, 2006, pp. 1568-1571.
18. E. Talu, K. Hettiarachchi, S. Zhao, R. L. Powell, A. P. Lee, M. L. Longo and P. A. Dayton, *Molecular Imaging*, 2007, 6, 384-392.
19. K. Hettiarachchi, E. Talu, M. L. Longo, P. A. Dayton and A. P. Lee, *Lab on a Chip*, 2007, 7, 463-468.
20. E. Talu, K. Hettiarachchi, R. L. Powell, A. P. Lee, P. A. Dayton and M. L. Longo, *Langmuir*, 2008, 24, 1745-1749.
21. M. M. Lozano and M. L. Longo, *Langmuir*, 2009, 25, 3705-3712.
22. J. I. Park, Z. Nie, A. Kumachev and E. Kumacheva, *Soft Matter*, 2010, 6, 630-634.
23. J. Il Park, E. Tumarkin and E. Kumacheva, *Macromolecular Rapid Communications*, 2010, 31, 222-227.
24. M. Seo, I. Gorelikov, R. Williams and N. Matsuura, *Langmuir*, 2010, 26, 13855-13860.
25. C. Jiang, X. Li, F. Yan, Z. Wang, Q. Jin, F. Cai, M. Qian, X. Liu, L. Zhang and H. Zheng, *Micro & Nano Letters*, 2011, 6, 417-421.
26. J. I. Park, D. Jagadeesan, R. Williams, W. Oakden, S. Chung, G. J. Stanisz and E. Kumacheva, *Acs Nano*, 2010, 4, 6579-6586.
27. M. H. Lee, V. Prasad and D. Lee, *Langmuir*, 2010, 26, 2227-2230.
28. K. Hettiarachchi, A. P. Lee, S. Zhang, S. Feingold and P. A. Dayton, *Biotechnology Progress*, 2009, 25, 938-945.
29. K. Hettiarachchi and A. P. Lee, *Journal of Colloid and Interface Science*, 2010, 344, 521-527.
30. C. Jiang, X. Li, Q. Jin, T. Chen, Z. Wang and H. Zheng, *IEEE*, 2010, 1-4.
31. S. Srivastava, A. Santos, K. Critchley, K.-S. Kim, P. Podsiadlo, K. Sun, J. Lee, C. Xu, G. D. Lilly, S. C. Glotzer and N. A. Kotov, *Science*, 2010, 327, 1355-1359.
32. S. Ho, K. Critchley, G. D. Lilly, B. Shim and N. A. Kotov, *Journal of Materials Chemistry*, 2009, 19, 1390-1394.
33. Z. Li, C. Dong, L. Tang, X. Zhu, H. Chen and J. Ren, *Luminescence*, 2011, 26, 439-448.
34. T. Faez, D. Goertz and N. De Jong, *Ultrasound in Medicine and Biology*, 2011, 37, 338-342.
35. P. Garstecki, A. M. Ganan-Calvo and G. M. Whitesides, *Bulletin of the Polish Academy of Sciences*, 2005, 53, 361-372.
36. A. M. Ganan-Calvo and J. M. Gordillo, *Physical Review Letters*, 2001, 87, 274501 274501-274504.
37. J. E. McKendry, C. A. Grant, B. R. Johnson, P. Coletta, J. Evans and S. D. Evans, *Bubble Science Engineering Technology*, 2010, 2, 48-54.
38. E. Buchner Santos, J. Morris, E. Glynos, V. Sboros and V. Koutsos, *Langmuir*, 2012, 28, 5753-5760.
39. C. A. Grant, J. E. McKendry and S. D. Evans, *Soft Matter*, 2012, 8, 1321-1326.

The invention claimed is:
1. A microfluidic apparatus for generating microbubbles, the apparatus comprising a nozzle having an entry orifice and extending along a longitudinal axis from the orifice to define a microbubble flow direction, the nozzle having a width and a height dimension which both increase in the bubble flow direction and one or more gas flow conduits and one or more liquid flow conduits.
2. The microfluidic apparatus for generating microbubbles according to claim 1, further comprising a contact chamber, the contact chamber including the orifice and the orifice being in communication with the nozzle along which, in use, bubbles flow.
3. The microfluidic apparatus according to claim 2, further comprising one or more secondary liquid flow conduits to carry a further liquid component.
4. The microfluidic apparatus according to claim 2, further comprising a source of gas and a gas flow controller to control flow of the gas to the contact chamber, and a source of liquid and a liquid flow controller to control flow of said liquid to the contact chamber.

5. The microfluidic apparatus according to claim 2, wherein the apparatus is configured to produce microbubbles in a microspray regime.

6. The microfluidic apparatus according to claim 5, configured such that in use a bulb of gas extends from the gas flow conduit through the orifice and into the nozzle.

7. The microfluidic apparatus according to claim 6, wherein the gas bulb extends to a region where the height and width dimensions of the nozzle increase.

8. A method of generating a population of microbubbles, the method comprising the step of using a nozzle having an entry orifice and extending along a longitudinal axis from the orifice to define a microbubble flow direction, the nozzle having a width and a height dimension which both increase in the bubble flow direction.

9. The method of claim 8, further comprising the steps of providing an apparatus comprising one or more gas flow conduits, one or more liquid flow conduits, and a contact chamber, the contact chamber including the orifice and the orifice being in communication with the nozzle along which, in use, bubbles flow and providing a microbubble forming liquid via the at least one liquid flow conduit and a gas via the at least one gas flow conduit.

10. The method of claim 9, wherein the microbubble forming liquid comprises a lipid, protein or polymer suitable to form a microbubble shell.

11. The method of claim 9, further comprising the step of providing the gas and microbubble forming liquid in such a manner that a bulb of gas formed in the contact chamber extends into the orifice between the contact chamber and the nozzle, and thereby forms microbubbles in the nozzle.

12. The method of claim 11, wherein the bulb of gas extends through the orifice into the nozzle.

13. The method of claim 8, wherein the population of microbubbles generated has a mean diameter of 10 pm or less.

14. The method of claim 8, wherein the microbubble forming liquid is provided at a flow rate of from 1 to 100 $\mu L/min^{-1}$.

15. The method of claim 8, wherein a gas is provided via one or more of the gas flow conduits at a pressure of from 1 to 100 psi.

16. The method of claim 8, further comprising the step of providing a linker moiety to the microbubbles.

17. The method of claim 8, further comprising the step of providing liposomes to the microbubbles.

18. The method of claim 8, further comprising the step of providing a hydrophobic liquid phase such that the microbubbles comprise the hydrophobic liquid phase.

19. The method of claim 18, wherein the hydrophobic liquid phase comprises a layer of lipid inside the shell of the microbubble.

20. The method of claim 19, wherein the hydrophobic liquid phase comprises droplets linked to the microbubble.

21. The method of claim 8, further comprising the step of providing an active agent to the microbubbles.

22. The method of claim 8, further comprising the step of providing a targeting moiety to the microbubbles.

23. The method of claim 8, further comprising the step of providing a label to the microbubble.

24. The method of claim 8, further comprising the step of providing one or more magnetic or charged particles to the microbubbles.

* * * * *